United States Patent [19]

Mitchell et al.

[11] Patent Number: 5,814,667

[45] Date of Patent: *Sep. 29, 1998

[54] USE OF NITRIC OXIDE-RELEASING COMPOUNDS AS HYPOXIC CELL RADIATION SENSITIZERS

[75] Inventors: James B. Mitchell, Damascus; Angelo Russo, Bethesda; Murali C. Krishna, Derwood; David A. Wink, Jr., Hagerstown, all of Md.; James E. Liebmann, Albuquerque, N. Mex.

[73] Assignee: United States of America as represented by the Department of Health and Human Services, Washington, D.C.

[*] Notice: The term of this patent shall not extend beyond the expiration date of Pat. No. 5,650,442.

[21] Appl. No.: 814,419

[22] Filed: Mar. 11, 1997

Related U.S. Application Data

[60] Division of Ser. No. 319,888, Oct. 7, 1994, Pat. No. 5,650,442, which is a continuation-in-part of Ser. No. 133,574, Oct. 8, 1993, abandoned.

[51] Int. Cl.⁶ .......................... A61K 31/13; A61K 31/44; A61K 31/495; A61K 31/445
[52] U.S. Cl. .................. 514/611; 514/149; 514/238.2; 514/255; 514/315; 514/319; 514/329; 514/332; 514/357; 514/476; 514/492; 514/494; 514/499; 514/558; 514/564; 514/563; 514/579; 514/610; 514/645; 514/649; 514/647
[58] Field of Search ....................... 514/611, 149, 514/238.2, 255, 315, 319, 329, 332, 357, 476, 492, 494, 499, 558, 564, 563, 579, 610, 645, 649, 647

[56] References Cited

U.S. PATENT DOCUMENTS 5,650,442  7/1997  Mitchell et al. ...................... 514/611

*Primary Examiner*—Keith D. MacMillan
*Attorney, Agent, or Firm*—Leydig, Voit & Mayer, Ltd.

[57] ABSTRACT

The present invention provides a method for sensitizing hypoxic cells in a tumor to radiation, wherein nitric oxide is delivered to target hypoxic cells through the administration of a nitric oxide-containing compound that spontaneously releases nitric oxide under physiological conditions without requiring the presence of oxygen. Also provided are methods of protecting noncancerous cells or tissues in a mammal from radiation, sensitizing cancerous cells in a mammal to chemotherapeutic agents, and protecting noncancerous cells or tissues in a mammal from chemotherapeutic agents, all by administration of the same compounds.

6 Claims, 11 Drawing Sheets

USE OF NITRIC OXIDE-RELEASING COMPOUNDS AS HYPOXIC CELL RADIATION SENSITIZERS

This is a divisional of applications Ser. No. 08/319,888, filed on Oct. 7, 1994 now U.S. Pat. No. 5,650,442 which application is a continuation-in-part of application Ser. No. 08/133,574, filed Oct. 8, 1993 abandoned.

TECHNICAL FIELD OF THE INVENTION

The present invention is directed to a method of using nitric oxide-containing compounds that spontaneously release nitric oxide under physiological conditions without requiring the presence of oxygen to sensitize hypoxic cells in a tumor to radiation. The present invention is also directed to methods of using the same nitric oxide-releasing compounds to protect noncancerous cells or tissues from radiation, to sensitize cancerous cells to chemotherapeutic agents, and to protect noncancerous cells or tissues from chemotherapeutic agents.

BACKGROUND OF THE INVENTION

Most human tumors are treated locally with ionizing radiation. Despite advances in the complex development and use of high energy linear accelerators, intricate computer-assisted treatment planning systems, which maximize the dose of radiation administered to a tumor, and the use of different and, perhaps, more efficient types of radiation, such as high linear energy transfer (LET) radiation, local control for a vast number of solid tumors has not substantially improved.

Over the past 50 years, radiobiologists have sought to gain a better understanding of the biological and physiological factors of tumors that might be important and exploitable in improving radiation-based cancer treatment. The biological characteristics of human tumors, however, are complex and poorly understood.

Oxygen has long been known to enhance the effectiveness of radiation. The presence of oxygen was shown to enhance the killing of cells in culture with X-rays by a factor of 2–3 (Howard-Flanders, *Nature*, 180, 1191–1192 (1957)). In other words, if cells are irradiated in an aerobic (~20% oxygen) as opposed to hypoxic (<0.5% oxygen) environment, they are 2–3 times more susceptible to the cytotoxic effects of radiation. The term Oxygen Enhancement Ratio (OER) is used to describe the decreased radiosensitivity of cells under hypoxic conditions as opposed to aerobic conditions. The OER for mammalian cells exposed to X-rays under aerobic conditions is about 1, while the OER for mammalian cells exposed to X-rays under hypoxic conditions is about 2–3, representing the fact that hypoxic cells are about 2–3 times more resistant, i.e., less susceptible, to the cytotoxic effects of radiation as compared to aerobic cells.

It has been postulated that radiation produces carbon-centered radicals, probably in the cellular DNA, that can react with molecular oxygen, which is a diradical molecule, to yield a lesion that is toxic and, if not repaired, will result in cell death (von Sonntag, *The Chemical Basis of Radiation Biology*, Taylor and Francis, eds., London, 1987). Under hypoxic conditions, very few, if any, oxygen-related lesions are formed, and, hence, there is less cell killing.

In 1956, Thomlinson and Gray (*Br. J. Cancer*, 9, 539–549 (1955)) observed in biopsied tumors taken from lung cancer patients that distinct regions of viable tumors were always near or surrounding blood capillaries. Regions of necrosis were found with increasing distances from the capillaries. Based on these observations, Thomlinson and Gray calculated that the maximum distance that oxygen could diffuse through actively metabolizing tissue was between 150 and 200 $\mu$m. This distance coincided with actual measurements of biopsied tissue. This led Thomlinson and Gray to hypothesize that a gradient of oxygen concentration may exist as a function of distance from capillaries and that tumor cells located at 150–200 $\mu$m away, while still viable, are in an environment of extremely low oxygen concentration. Such cells were considered to be resistant to radiation and their presence was thought to limit the effectiveness of radiation cancer treatment. Powers and Tolmach (*Nature*, 197, 710–711 (1963)) quantitatively showed, using a rat tumor model, that viable radiation-resistant hypoxic cells do exist in vivo.

The success of the local treatment of many cancerous tumors with ionizing radiation is believed to be limited by the presence of hypoxic cell subpopulations within the tumor (Thomlinson and Gray, supra; Powers and Tolmach, supra; and Gatenby et al., *Int. J. Radiat. Oncol. Biol. Phys.*, 14, 831–838 (1988)). Given that hypoxic cells are approximately three-fold more resistant to radiation than aerobic cells, a major research objective of radiation oncology and biology has been to identify approaches to sensitize and eliminate hypoxic cells from tumors (Hall, "The oxygen effect and reoxygenation," in *Radiobiology for the Radiologist*, J. B. Lippincott Co., Philadelphia, Pa., pp. 137–160 (1988)). The goal has been to identify an approach that will reduce the OER from about 3.0 to about 1.0, i.e., so that hypoxic cells will have the same response to radiation as aerobic cells.

Over the course of 25 years, various in vitro systems have been used to evaluate agents for their potential to sensitize hypoxic cells to radiation (Hall et al., *Br. J. Radiol.*, 39, 302–307 (1966); Bedford et al., *Br. J. Radiol.*, 39, 896–900 (1966)). Such studies have demonstrated that nitric oxide gas sensitizes hypoxic bacterial cells to ionizing radiation (Howard-Flanders, supra). Nitric oxide (NO), which is non-toxic in the absence of radiation, was shown to have an affinity similar to that of oxygen and to "fix" radiation-induced carbon-centered radicals in DNA.

NO also has been shown to have vasodilatory effects on vasculature (Ignarro, *Annu. Rev. Pharmacol. Toxicol.*, 30, 535–560 (1990)). Tumor blood flow was selectively reduced in tumor versus normal tissue by the administration of nitric oxide synthase, an enzyme that generates NO (Andrade et al., *Brit. J. Pharm.*, 104, 1092–1095 (1992)). In vivo studies have demonstrated, though, that the administration of high concentrations of NO gas to hypoxic cell targets has serious drawbacks, including damage to the lungs and the destruction of NO prior to arrival at the target cells by other chemical reactions, such as the diffusion-controlled oxidation of oxyhemoglobin in the blood. Accordingly, although NO gas may be of limited utility in the local treatment of lung tumors, its usefulness in the treatment of distant solid tumor sites is limited by an inability to deliver adequate concentrations of NO to the target site.

High LET radiation, i.e., neutron irradiation, has been proposed as an alternative to X-rays because hypoxic cells are less resistant to neutron radiation (OER=1.7) than x-rays (Hall, in *Radiobiology for the Radiologist*, J. B. Lippincott Co., Philadelphia, Pa., pages 161–177 (1988)). The use of neutrons in clinical radiotherapy, however, has not yielded significant improvement in tumor response and, due to the cost of constructing and maintaining a clinical neutron facility, probably will not be given further consideration.

The use of hyperbaric oxygen in the treatment of tumors also has been evaluated, both experimentally and clinically. Basically, hyperbaric oxygen (100%) is forced into hypoxic regions of tumors. This approach has shown some degree of hypoxic radiosensitization in rodent tumors (Powers and Tolmach, supra). However, multiple hyperbaric oxygen treatments, i.e., 20–30, are required, and very few patients have accrued for clinical trials.

Another approach that has received attention is the development of chemicals, in particular nitroimidazoles, which are not metabolized, like oxygen, but diffuse into hypoxic regions in tumors and sensitize the hypoxic cells to radiation (Adams et al., Radiat. Res., 67, 9–20 (1976)). At concentrations of about 1 mM, nitroimidazoles have been shown to radiosensitize (OER=1.6) hypoxic cells but not aerobic cells. The mechanism of hypoxic cell radiosensitization by nitroimidazoles is unknown. However, it is hypothesized that nitroimidazoles have similar electron affinity to that of oxygen and that, under hypoxic conditions, they can react with carbon-centered free radicals produced by radiation and, like oxygen, "fix" the damage on molecules that are necessary for cell survival. Two nitroimidazoles, namely misonidazole and SR-2508, have been introduced into clinical radiotherapy trials. Misonidazole was shown to be toxic to normal tissues, causing peripheral neuropathy, which limits the effective dosage (Phillips et al., Cancer Treat. Rep., 68, 291–301 (1984)). SR-2508 was specifically synthesized to circumvent this problem, and patients are currently being accrued to evaluate it as a hypoxic cell radiation sensitizer (Coleman et al., Int. J. Radiat. Oncol. Biol. Phys., 12, 1105–1108 (1986)).

An NO releasing agent, namely SIN-1, has been described as an agent that enhances the radiation sensitivity of a transplantable murine tumor (Wood et al., Biochem. Biophys. Res. Commun., 192, 505–510 (1993)). However, its usefulness as a hypoxic radiosensitizer is limited by its dependence on the presence of oxygen (Feelisch et al., J. Cardiovasc. Pharmacol., 14 (Suppl. 11), S13–S22 (1989); Bohn et al., J. Cardiovasc. Pharmacol. 14 (Suppl. 11), S6–S12 (1989)).

Adams et al. (supra) found that a correlation existed between the radiosensitizing activity of various nitroaromatic and nitroheterocyclic compounds and their electron affinity. Nitrobenzoyl derivatives of spermine and spermidine were shown to have increased hypoxic cell radiosensitization over misonidazole. The radiosensitizing activity was found to be attributable to the nitrobenzoyl group only, given that spermine and spermidine without the nitrobenzoyl group failed to demonstrate any sensitizing properties whatsoever (Murayama et al., Int. J. Radiat. Biol. Relat. Stud. Phys. Chem. Med., 44, 497–503 (1983)). The usefulness of nitrobenzoyl derivatives of spermine and spermidine, however, is limited to a certain degree by relatively short half-lives in solution.

In view of the inadequacy of the various treatment modalities currently available to overcome the decreased sensitivity of hypoxic tumor cells to radiation, there remains a need for a method of sensitizing hypoxic cells to radiation. It is an object of the present invention to provide such a method. It is a related object of the present invention to provide a method of delivering nitric oxide to hypoxic cells in a tumor. It is another object of the present invention to provide a method of delivering nitric oxide to hypoxic cells by means of an agent, in particular a water-soluble agent, that spontaneously releases NO under physiological conditions without requiring the presence of oxygen. It is a further object of the present invention to provide for such delivery in a controlled and predictable manner.

Another object of the present invention is to provide a method of protecting noncancerous cells or tissues from radiation. It is a related object of the present invention to provide a method of delivering nitric oxide to noncancerous cells or tissues. It is another object of the present invention to provide a method of delivering nitric oxide to noncancerous cells or tissues by means of an agent, in particular a water-soluble agent, that spontaneously releases NO under physiological conditions without requiring the presence of oxygen. It is a further object of the present invention to provide for such delivery in a controlled and predictable manner.

Yet another object of the present invention is to provide a method of sensitizing cancerous cells to chemotherapeutic agents. It is a related object of the present invention to provide a method of delivering nitric oxide to cancerous cells. It is another object of the present invention to provide a method of delivering nitric oxide to cancerous cells by means of an agent, in particular a water-soluble agent, that spontaneously releases NO under physiological conditions without requiring the presence of oxygen. It is a further object of the present invention to provide for such delivery in a controlled and predictable manner. A further object of the present invention is to provide a method of protecting noncancerous cells or tissues from chemotherapeutic agents. It is a related object of the present invention to provide a method of delivering nitric oxide to noncancerous cells or tissues. It is another object of the present invention to provide a method of delivering nitric oxide to noncancerous cells or tissues by means of an agent, in particular a water-soluble agent, that spontaneously releases NO under physiological conditions without requiring the presence of oxygen. It is a further object of the present invention to provide for such delivery in a controlled and predictable manner. These and other objects and advantages of the present invention, as well as additional inventive features, will be apparent from the description of the invention provided herein.

BRIEF SUMMARY OF THE INVENTION

The present invention provides a method for sensitizing hypoxic tumor cells to radiation, wherein nitric oxide is delivered to target hypoxic cells in a tumor in a controlled and predictable manner through the administration of a nitric oxide-containing compound, which spontaneously releases nitric oxide under physiological conditions without requiring the presence of oxygen, prior to the administration of radiation to the hypoxic tumor cells. Also provided is a method for protecting noncancerous cells or tissues from radiation, wherein nitric oxide is delivered to noncancerous cells or tissues in a controlled and predictable manner through the administration of one of the same nitric oxide-containing compounds prior to the administration of radiation. Methods of sensitizing cancerous cells to chemotherapeutic agents and protecting noncancerous cells or tissues from chemotherapeutic agents are also provided.

DETAILED DESCRIPTION OF THE PREFERRED EMBODIMENTS

Figure 1A:
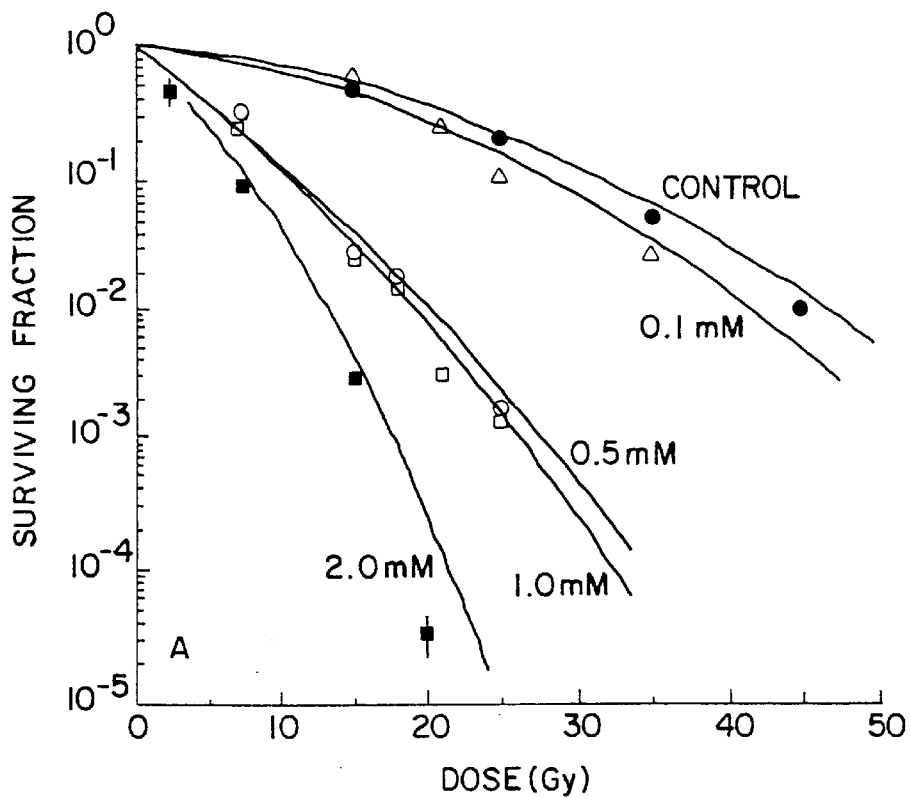
FIGS. 1A and 1B are graphs of surviving fraction versus radiation dose (Gy) showing the radiation survival curves for V79 fibroblasts exposed to various concentrations of DEA/NO or DEA/NO decomposition products under hypoxic (metabolic induction) and aerobic conditions, respectively.

It has been surprisingly discovered that nitric oxide-containing compounds that spontaneously release NO under physiological conditions without requiring the presence of oxygen can be used to sensitize hypoxic cells in a tumor to ionizing radiation. The present invention provides a method of sensitizing hypoxic cells in a tumor in a mammal to ionizing radiation administered during radiotherapy. The present inventive method comprises administering to a mammal having a tumor containing hypoxic cells a radiation-sensitizing effective amount of a nitric oxide-containing compound that spontaneously releases nitric oxide under physiological conditions without requiring the presence of oxygen prior to radiotherapy. Various nitric oxide-containing compounds can be used in the context of the present inventive method.

Recently, for example, a series of amine derivatives of dimeric nitric oxide (NONOates) have been shown to release nitric oxide in a predictable manner under physiological conditions (Maragos et al., *J. Med. Chem.*, 34, 3242–3247 (1991)). The half-lives of the NONOates can range from 1 minute to several days (Hrabie et al., *J. Org. Chem.*, 58, 1472–1476 (1993)) and, accordingly, offer advantages over compounds, such as spermidine and spermine, by having characteristically prolonged half-lives in solution. These compounds have been employed in various studies of cytostasis (Maragos et al., *Cancer Res.*, 53, 564–568 (1993)), cytotoxicity, mutagenicity (Wink et al., *Science*, 254, 1001–1003 (1991)), nitric oxide-mediated dopamine release in nerve cell cultures, and nitric oxide-mediated inhibition of platelet aggregation (Keefer et al. "Complexes of nitric oxide with nucleophiles as agents for the controlled biological release of nitric oxide," in *Biology of Nitric Oxide, 2, Enzymology, Biochemistry, Immunology*, Moncada et al., eds., Portland Press, Chapel Hill, N.C., pages 153–156, (1992)). Vasorelaxation of aortic ring strips was shown to correlate linearly to the concentration of nitric oxide release from the NONOates (Maragos et al., supra). NONOates also have been shown to be effective in the treatment of cardiovascular disorders and hypertension (U.S. Pat. Nos. 4,954,526, 5,155,137, and 5,212,204 and WO 93/07114) and have been suggested to be effective in cancer chemotherapy (Maragos et al. (1993), supra). The potential utility of these compounds in other biomedical applications also has been suggested (Maragos et al. (1991), supra; Keefer et al. (1992), supra). Such NONOates have been found to be useful in the context of the present invention, and, thus, the present inventive method of sensitizing hypoxic cells in a tumor in a mammal to ionizing radiation includes the administration to a mammal having a tumor containing hypoxic cells a radiation-sensitizing effective amount of a compound of the formula:

$$[R_1N(R_2)N(NO)O]_yX \qquad \text{(Formula I)}$$

wherein $R_1$ and $R_2$ are the same or different and are selected from the group consisting of hydrogen, a $C_1$–$C_8$ alkyl, a $C_3$–$C_{10}$ aryl, a $C_4$–$C_{10}$ heterocyclic nitrogen-containing radical, a $C_3$–$C_{10}$ aryl substituted with a $C_1$–$C_3$ alkyl, and a $C_3$–$C_{10}$ cycloalkyl, either or both of which R groups may be substituted by 1–3 substituents, which may be the same or different and are selected from the group consisting of halo, hydroxy, $C_1-C_8$ alkoxy, amino, amido, formyl, carboxy, and nitro, with the proviso that both $R_1$ and $R_2$ cannot be hydrogen; and wherein X is a pharmaceutically acceptable cation, a pharmaceutically acceptable metal center, or a pharmaceutically acceptable organic group selected from the group consisting of a $C_1-C_8$ alkyl, acyl, and amido; and wherein Y is 1 to 3 and is consistent with the valence of X, prior to radiotherapy. In some cases, it may be desirable to administer the compound during radiotherapy in addition to or as an alternative to prior administration.

The term "sensitizing" means increasing sensitivity. The term "$C_1-C_8$ alkyl" is used to refer to branched and straight chain hydrocarbon radicals of 1–8 carbons, such as methyl, ethyl, propyl, isopropyl, butyl, 2-butyl, tert-butyl, amyl, isoamyl, hexyl, heptyl, octyl, and the like. The term "$C_3-C_{10}$ aryl" is used to refer to aromatic cyclic hydrocarbon radicals of 3–10 carbons, such as phenyl, naphthyl and the like, and the term "$C_4-C_{10}$ heterocyclic nitrogen-containing radical" is used to refer to radicals such as pyrrolyl, pyridinyl, quinolinyl, isoquinolinyl, and the like. Similarly, "$C_3-C_1$ cycloalkyl" is used to refer to nonaromatic cyclic hydrocarbon radicals of 3–10 carbons, such as cyclopropyl, cyclopentyl, cyclohexyl, cycloheptyl, cyclooctyl, and the like. The terms "halo" and "halogen" are intended to include fluorine, chlorine, bromine, and iodine. Other terms should be given those meanings normally ascribed to such terms by those of skill in the art.

The term "pharmaceutically acceptable cation" as used herein means any cation biologically compatible in a mammal and includes alkylammonium cations, e.g., isopropyl ammonium cation and the like; alkali metals, e.g., sodium, potassium, lithium, and the like; and alkaline earth metals, e.g., calcium, barium, magnesium, and the like. The only essential characteristic of the cation chosen is that it not be biologically incompatible in a mammal.

The term "pharmaceutically acceptable metal center" as used herein means a central metal ion, having a valence of 1 to 3 attached by coordinate links to one or more nonmetal atoms of each of the Y organic groups of the above formula. The term "central metal ion" as used herein includes biologically acceptable metal ions selected from alkali metals, such as sodium, potassium, lithium, and the like; alkaline earth metals, such as calcium, magnesium, barium, and the like; transition metals, including iron, copper, nickel, zinc, and the like; Group III metals including aluminum and the like, and lanthanide series metals. The only principal requirement for the central metal ion chosen is biological compatibility in a mammal.

The term "pharmaceutically acceptable organic group" as used herein refers to those biologically acceptable organic groups that covalently bond to the organic grouping of the compound of the above formula to form ethers and other derivatives thereof. Acceptable organic groups include lower alkyls, acyl, amido, and the like.

Other nitric oxide-releasing compounds useful in the context of the present inventive method, in addition to those of Formula I, include the nitric oxide-releasing compounds of Formulas II, III and IV:

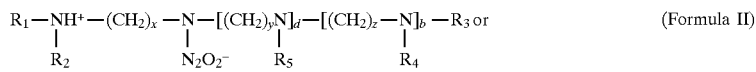

(Formula II)

(Formula III)

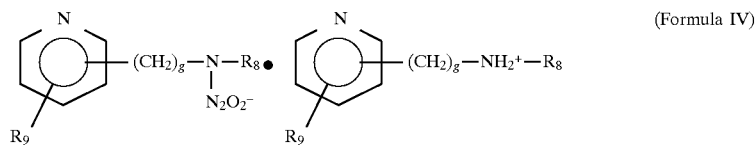

(Formula IV)

wherein b and d are independently zero or one; x, y, and z are independently 2–12; $R_1-R_8$ are independently hydrogen, $C_3-C_8$ cycloalkyl, $C_1-C_{12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl; $R_9$ is hydrogen or a $C_1-C_{12}$ straight or branched chain alkyl; B is

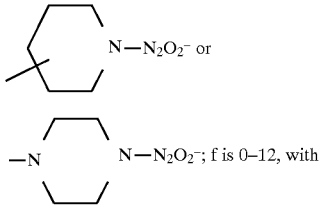

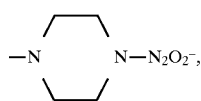

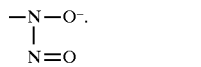

Preferred among the compounds of Formulas II and III are those compounds wherein $R_1-R_7$ are independently hydrogen, $C_{3-8}$ cycloalkyl, $C_{1-12}$ straight or branched chain alkyl, benzyl, or acetyl. More preferred are those compounds wherein $R_1-R_7$ are independently hydrogen, methyl, ethyl, benzyl or acetyl, and x, y and z are 2–4. Most preferred are those compounds wherein $R_1-R_7$ are independently hydrogen, methyl, benzyl or acetyl, and x, y and z are 2–4.

Preferred among the compounds of Formula IV are those compounds wherein $R_8$ is $C_{5-6}$ cycloalkyl, $C_{1-4}$ straight or branched chain alkyl, benzyl or acetyl. More preferred are those compounds wherein $R_8$ is methyl, ethyl, benzyl or acetyl, and most preferred are those compounds wherein $R_8$ is methyl or acetyl.

In addition to the nitric oxide-releasing compounds of Formulas I–IV, the following nitric oxide-releasing compounds can be used in conjunction with the present inventive method:

(Formula V)

wherein J is an organic or inorganic moiety, preferably a moiety which is not linked to the nitrogen of the $N_2O_2^-$ group through a carbon atom, $M^{+x}$ is a pharmaceutically acceptable cation, where x is the valence of the cation, a is 1 or 2, and b and c are the smallest integers that result in a neutral compound, preferably such that the compound is not a salt of alanosine or dopastin, as described in U.S. Pat. No. 5,212,204;

(Formula VI)

wherein $R_1$ and $R_2$ are independently selected from the group consisting of a straight chain or branched chain $C_1$–$C_{12}$ alkyl group and a benzyl group, with the proviso that no branch occur on the alpha carbon atom, or else $R_1$ and $R_2$ together with the nitrogen atom are bonded to form a heterocyclic group, preferably a pyrrolidino, piperidino, piperazino or morpholino group, $M^{+x}$ is a pharmaceutically acceptable cation, and x is the valence of the cation, as described in U.S. Pat. No. 5,039,705;

(Formula VII)

wherein M is a pharmaceutically acceptable metal, or, where x is at least two, a mixture of two different pharmaceutically acceptable metals, L is a ligand different from $(R^1R^2N-N_2O_2)$ and is bound to at least one metal, $R^1$ and $R^2$ are each organic moieties and may be the same or different (with the proviso that where M is copper, x is one, L is methanol, and y is one, that at least one of $R^1$ or $R^2$ is not ethyl), x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. patent application Ser. No. 07/858,885, filed Mar. 27, 1992; and

(Formula VIII)

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula $-(CH_2)_n-ON=N(O)NR_1R_2$, wherein n is an integer of 2–8, and $R_1$ and $R_2$ are as defined above; with the proviso that $R_1$, $R_2$ and $R_3$ do not contain a halo or a hydroxy substituent α to a heteroatom, as described in U.S. patent application Ser. No. 07/950,637, filed Sep. 22, 1992.

In addition to the nitric oxide-releasing compounds described above, other nitric oxide-containing compounds that spontaneously release NO under physiological conditions and do not require the presence of oxygen can be used in the present inventive method. These compounds include S-nitroso adducts of the formula O=N—S—R, wherein R is selected from the group consisting of a $C_1$–$C_8$ alkyl, a $C_3$–$C_{10}$ aryl, a $C_4$–$C_{10}$ heterocyclic nitrogen-containing radical, a $C_3$–$C_{10}$ aryl substituted with a $C_1$–$C_3$ alkyl, and a $C_3$–$C_{10}$ cycloalkyl, which R groups may be substituted by 1–3 substituents, which may be the same or different and are selected from the group consisting of halo, hydroxy, $C_1$–$C_8$ alkoxy, amino, amido, formyl, carboxy, and nitro. Preferred S-nitroso adducts include S-nitroso adducts of peptides and proteins, particularly S-nitroso-N-acetyl penicillamine (SNAP) (Morley et al., J. Cardiovasc. Pharmacol., 21, 670–676 (1993); Feelisch, J. Cardiovasc. Pharmacol., 17, S25–S33 (1991); Stamler et al., PNAS (USA), 89, 7674–7677 (1992); and Stamler et al., PNAS (USA), 89, 444–448 (1992)) and S-nitroso-glutathione (GSNO). Such adducts offer the advantages of cell-targeting methods, through the use of adducts of S-nitroso cell-specific antibodies such as S-nitroso antibody adducts that are specific for cancer cells and adducts of S-nitroso peptides that mimic recognition sequences of receptor ligands.

The present invention involves the use of the aforesaid nitric-oxide releasing compounds to reduce the Oxygen Enhancement Ratio (OER) of hypoxic cells, preferably to about 2 or less. More preferably, the present invention will provide for an OER of hypoxic cells of about 1.5 or less, most preferably of about 1.

The present invention also provides a method of protecting nonmalignant tissues or cells from radiation administered during radiotherapy. The method comprises administering to a mammal about to undergo radiotherapy a radiation-protecting effective amount of a compound as described above with respect to the other inventive method. In some cases, it may be desirable to administer the compound during radiotherapy in addition to or as an alternative to prior administration.

The present invention further provides a method of sensitizing cancerous cells to chemotherapeutic agents, such as alkylating agents, e.g., melphalan and thiotepa, bioreductive agents, e.g., mitomycin C and SR 4233, and DNA crosslinking agents, e.g., cisplatin, administered during chemotherapy. The method comprises administering to a mammal in need of chemotherapy a chemotherapy-sensitizing effective amount of a compound as described above with respect to the other inventive methods.

The present invention also provides a method of protecting noncancerous cells and tissues from chemotherapeutic agents administered during chemotherapy. The method comprises administering to a mammal in need of chemotherapy a chemotherapy-protecting effective amount of a nitric oxide-containing compound as described above.

The compounds used in the present inventive methods are characterized in that they are highly soluble in physiological solutions and release NO spontaneously without the need for enzymatic conversion. The release of NO, in particular the rate of release, can be controlled by the choice of the nucleophile moiety, is independent of the presence of oxygen, and is not accompanied by overtly toxic byproducts.

The compounds used in the present inventive methods may be synthesized according to methods that are well known in the art. It is preferred that appropriate amines be obtained from suitable commercial suppliers and reacted with nitric oxide under suitable conditions to obtain the desired compound. Suitable commercial suppliers include, among others, Aldrich Chemical Co., Milwaukee, Wis.

Once a suitable amine has been synthesized or otherwise obtained (e.g., from a commercial supplier), it may then be reacted with nitric oxide to obtain a compound for use in the present inventive methods. For example, one of the methods of Drago et al., *J. Am. Chem. Soc.*, 83, 1819–1822 (1961), may be used to react a suitable primary amine with nitric oxide. Certain diamines may be prepared in accordance with Garrido et al., *J. Org. Chem.*, 49, 2021–2023 (1984). Certain triamines may be prepared in accordance with Bergeron, *Accts. Chem. Res.*, 19, 105–113 (1986). Bergeron, in *J. Org. Chem.*, 53, 3108–3111 (1988), also describes various methods that may be used to prepare tetraamines. Carboni et al., *Tet. Let.*, 29, 1279–1282 (1988), discloses techniques that are relevant to the preparation of di-, tri-, and tetraamines. Other methods that may be employed in synthesis are described in U.S. Pat. Nos. 4,954,526 and 5,155,137.

Once a suitable amine has been prepared or commercially obtained, it may then be reacted with nitric oxide to produce one of the nitric oxide-containing compounds to be used in the present inventive methods. Suitable methods are described in the '526 and '137 patents, for example. If certain of the amines to be reacted with nitric oxide contain additional nitrogen, oxygen, or other heteroatoms, suitable blocking groups may be employed to prevent the reaction of such atoms with nitric oxide. The blocked heteroatoms may then be unblocked after the Drago reaction of the amine with nitric oxide. Such blocking/deblocking agents and methods of using them are known in the art.

Once the desired nitric oxide adduct has been prepared, a pharmaceutically acceptable salt thereof can be prepared, if desired. For example, the potassium salt of one of the compounds can be prepared by reacting the compound with potassium hydroxide in ethanol or similar solution. Alternatively, sodium, calcium, and magnesium salts, among others, can be prepared.

The compounds of the present inventive methods can be used as is or in the form of their pharmaceutically acceptable salts and derivatives, and can be used alone or in appropriate combination with one or more other compounds/derivatives of the present invention or other active compounds. It should be understood, however, that the salt or derivative should not be one that renders the compound unstable or insoluble in water or toxic at the doses contemplated.

S-nitroso adducts of peptides and proteins form readily as described in the art. See, for example, the two papers by Stamler et al., supra.

The nitric-oxide releasing compounds can also be incorporated into a polymeric matrix as described in U.S. patent application Ser. No. 07/935,565. Incorporation of the $N_2O_2^-$ functional group into a polymeric matrix provides a polymer-bound nitric oxide/nucleophile adduct composition that can be applied with specificity to a biological target site. Site-specific application of a polymer-bound adduct enhances the selectivity of action of the nitric oxide releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue. Similarly, attachment of $N_2O_2^-$ groups to small peptides that mimic the recognition sequences of ligands for important receptors provides localized concentrated effect of nitric oxide release, as would attachment to oligonucleotides capable of site-specific interactions with target sequences in a nucleic acid.

Additionally, incorporation of the $N_2O_2^-$ functional group into a polymer matrix can reduce the propensity of the nitric oxide/nucleophile adduct for the relatively rapid release of nitric oxide. This prolongs the release of nitric oxide by the $N_2O_2^-$ functional group, and allows for efficient dosing to achieve a desired biological effect so the frequency of dosing can be reduced.

While not being bound to any particular theory, it is believed that longevity of nitric oxide release in the polymer-bound nitric oxide/nucleophile adduct compositions of the present invention is to be attributed both to the physical structure of the composition and to electrostatic effects. Thus, it is believed that if the polymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the half-life of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$- catalyzed decomposition. For example, by attaching amino groups to the polymeric support that are capable of forming the nitric oxide-releasing $N_2O_2^-$ functional group on reaction with nitric oxide, partially converted structures can be produced on less-than-exhaustive treatment with nitric oxide that after exposure to water contain a large number of positively charged ammonium centers surrounding the $N_2O_2^-$ group that electrostatically inhibit the approach of $H^+$ ions capable of initiating nitric oxide loss from the nitric oxide releasing $N_2O_2^-$ functional group.

The nitric oxide-releasing $N_2O_2^-$ functional groups that are bound to the polymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide releasing $X[N(O)NO]^-$ group in the vicinity of the particular cells of interest. As an example, covalent attachment of a protecting group to the anionic $[N(O)NO]^-$ function provides a means of postponing nitric oxide release until the molecule reaches an organ capable of metabolically removing the protecting group. By choosing a protecting group that is selectively cleaved by enzymes specific to a tumor, biological disorder, cell, or tissue of interest, for example, the action of the nitric oxide/nucleophile complex can be targeted to maximize the desired effect. While the polymer-bound nitric oxide releasing compositions of the present invention are capable of releasing nitric oxide in an aqueous solution, such a compound preferably releases nitric oxide under physiological conditions.

The nitric oxide releasing $N_2O_2^-$ functional group for attachment to a polymer is preferably a nitric oxide/nucleophile adduct, e.g., a complex of nitric oxide and a nucleophile, most preferably a nitric oxide/nucleophile complex which contains the anionic moiety $X[N(O)NO]^-$, where X is any suitable nucleophile residue. The nucleophile residue is preferably that of Formula I, such as a primary (e.g., X=(CH$_3$)$_2$CHNH, as in (CH$_3$)$_2$CHNH[N(O)NO]Na) or secondary amine (e.g., X=(CH$_3$CH$_2$)$_2$N, as in (CH$_3$CH$_2$)$_2$N[N(O)NO]Na), or a polyamine (e.g., X=spermine, as in the zwitterion H$_2$N(CH$_2$)$_3$NH$_2$$^+$(CH$_2$)$_4$N [N(O)NO]$^-$(CH$_2$)$_3$NH$_2$, or X=3-(n-propylamino) propylamine, as in the zwitterion CH$_3$CH$_2$CH$_2$N[N(O)NO] $^-$CH$_2$CH$_2$CH$_2$NH$_3$$^+$), or a derivative thereof. Such nitric oxide/nucleophile complexes are stable solids and are capable of delivering nitric oxide in a biologically usable form at a predictable rate.

The nucleophile residue for polymer attachment is preferably not an entity such as that of sulfite (e.g., X=SO$_3$$^-$, as in NH$_4$O$_3$S[N(O)NO]NH$_4$) even though the complex is a stable compound, since it is capable of releasing nitric oxide in an aqueous environment only under harsh, nonphysiological conditions.

Other suitable nitric oxide/nucleophile complexes for attachment to a polymer include those having the formulas of Formulas II–VIII above.

Any of a wide variety of polymers can be used in the context of the present invention. It is only necessary that the polymer selected is biologically acceptable. Illustrative of polymers suitable for use in the present invention are polyolefins, such as polystyrene, polypropylene, polyethylene, polytetrafluorethylene, polyvinylidene difluoride, polyvinylchloride, derivatized polyolefins such as polyethylenimine, polyethers, polyesters, polyamides such as nylon, polyurethanes, biopolymers such as peptides, proteins, oligonucleotides, antibodies and nucleic acids, starburst dendrimers, and the like.

The physical and structural characteristics of the polymers suitable for use in the present invention are not narrowly critical, but rather will depend on the end use application. It will be appreciated by those skilled in the art that where the polymer-bound nitric oxide/nucleophile adduct compositions of the present invention are intended for topical, dermal, percutaneous, or similar use, they need not be biodegradable. For some uses, such as ingestion or the like, it may be desirable that the polymer of the polymer-bound compositions slowly dissolves in a physiological environment or that it is biodegradable.

The nitric oxide-releasing complexes having N$_2$O$_2$$^-$ functional groups, including the compounds described above, may be bound to the polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent.

Alternatively, nitric oxide releasing N$_2$O$_2$$^-$ functional groups may be bound to the polymer by formation of a nitric oxide/nucleophile complex of the types and having the formulas of those described above, in situ on the polymer. The N$_2$O$_2$$^-$ functional group may be attached to an atom in the backbone of the polymer, or it may be attached to a group pendant to the polymer backbone, or it may simply be entrapped in the polymer matrix. Where the N$_2$O$_2$$^-$ functional group is in the polymer backbone, the polymer includes in its backbone sites which are capable of reacting with nitric oxide to bind the nitric oxide for future release. For example, where the polymer is polyethylenimine, the polymer includes nucleophilic nitrogen atoms which react with nitric oxide to form the N$_2$O$_2$$^-$ functional group at the nitrogen in the backbone. Where the N$_2$O$_2$$^-$ functional group is a group pendant to the polymer backbone, the polymer contains, or is derivatized with, a suitable nucleophilic residue capable of reacting with nitric oxide to form the N$_2$O$_2$$^-$ functionality. Reaction of the polymer which contains a suitable nucleophilic residue, or of the suitably derivatized polymer with nitric oxide thus provides a polymer-bound nitric oxide-releasing N$_2$O$_2$$^-$ functional group. To form the polymer-bound nitric oxide releasing N$_2$O$_2$$^-$ functional group, it is generally preferred to impart a net charge to the polymer near the site on the polymer where the N$_2$O$_2$$^-$ functional group is to be formed. The resulting polymer bound nitric oxide-releasing compounds may then be administered as described below or may be formed into an implant for implantation in or near a tumor, for example.

The present inventive methods can be utilized in vitro for scientific and research purposes. However, the methods of the present invention have particular usefulness in in vivo applications, namely radiosensitization, radioprotection, chemotherapy sensitization, and chemotherapy protection. The radiosensitization method is believed to accomplish the objective of sensitizing hypoxic cells in tumors to radiation by fixing damage generated by X-irradiation, such as carbon-centered free radicals in DNA, when electrons are transferred from the free radicals to NO. The NO is also believed to increase blood flow in the tumor, thereby increasing oxygenation and responsiveness to X-rays. The present inventive method includes the administration to a mammal, particularly a human, having a tumor comprising hypoxic cells, a radiation-sensitizing effective amount of one or more of the aforementioned compounds or pharmaceutically acceptable salts or derivatives thereof or polymers, alone or in combination with one or more other pharmaceutically active compounds, in a pharmaceutically acceptable composition prior to and/or during radiotherapy. It is believed that the radioprotection method protects noncancerous cells and tissues, such as bone marrow, during radiotherapy by increasing the therapeutic index (the ratio of the largest dose producing no toxic symptoms to the smallest dose routinely producing cures; a measure of the relative desirability of using a particular drug to attain a particular treatment) of the treatment modality.

With respect to both radiation methods and both chemotherapy methods, namely sensitization and protection, the nitric oxide-releasing compound or polymer should be administered prior to radiotherapy or chemotherapy, respectively, preferably from about 15 min to about 60 min prior to therapy. The amount of time required will depend, in part, upon the particular nitric oxide-releasing compound or polymer and the method of administration used. In some cases, it may be desirable to administer the nitric oxide-releasing compound or polymer during radiotherapy or chemotherapy, in addition to or as an alternative to prior administration.

One skilled in the art will appreciate that suitable methods of administering a compound useful in the context of the present invention to a mammal are available, and, although more than one route can be used to administer a particular compound, a particular route can provide a more immediate and more effective reaction than another route. Accordingly, the described methods are merely exemplary and are in no way limiting.

The dose administered to an animal, particularly a human, in the context of the present invention should be sufficient to effect the desired response, i.e., either increased radiation sensitivity of hypoxic cells in a tumor, increased radiation protection of noncancerous cells and tissues, increased sensitivity of cancerous cells to a chemotherapeutic agent, or increased protection of noncancerous cells and tissues from a chemotherapeutic agent, in the animal over a reasonable time frame. One skilled in the art will recognize that dosage will depend upon a variety of factors including the strength of the particular compound employed, the age, species, condition, and body weight of the animal, as well as the size of the tumor to be destroyed or the amount of noncancerous tissue to be protected. The size of the dose will also be determined by the route, timing and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of about 0.1 to about 100 mg of one or more of the compounds described above per kg body weight.

Furthermore, with respect to chemotherapy sensitization and protection, the determination of which NO-releasing compound, i.e., NONOate, to use in combination with a given chemotherapeutic agent can be done in accordance with the methods presented in the Examples. The choice of NONOate will depend, in part, on whether chemotherapy sensitization or protection is to be effected for the chemotherapeutic agent to be used in the context of a chemotherapeutic treatment regimen.

The present invention also provides a pharmaceutical composition comprising a pharmaceutically acceptable carrier and a radiation-sensitizing, radiation-protecting, chemotherapy-sensitizing or chemotherapy-protecting effective amount of one or more of the compounds or polymers useful in the present inventive methods. The carrier may be any of those conventionally used and is limited only by chemico-physical considerations, such as solubility and lack of reactivity with the compound, and by the route of administration. It will be appreciated by one of skill in the art that, in addition to the following described pharmaceutical composition, the compounds of the present inventive methods may be formulated as inclusion complexes, such as cyclodextrin inclusion complexes, or liposomes.

Examples of pharmaceutically acceptable acid addition salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulphonic, for example p-toluenesulphonic acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of excipient will be determined in part by the particular compound, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting. Injectable formulations are among those formulations that are preferred in accordance with the present inventive methods. The requirements for effective pharmaceutical carriers for injectable compositions are well known to those of ordinary skill in the art (See *Pharmaceutics and Pharmacy Practice*, J. B. Lippincott Company, Philadelphia, Pa., Banker and Chalmers, eds., pages 238–250, (1982), and *ASHP Handbook on Injectable Drugs*, Toissel, 4th ed., pages 622–630 (1986)). It is preferred that such injectable compositions be administered intravenously, intratumorally (within the tumor), or peritumorally (near the outside of the tumor). It will be appreciated by one of skill in the art that various of the described injectable compositions are suitable for intratumoral and peritumoral administration.

Topical formulations are well-known to those of skill in the art and are suitable in the context of the present invention for application to skin and hair as radiation protection.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds or polymers of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa, particularly with respect to radiation protection.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds and polymers useful in the present inventive methods may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The following examples further illustrate the present invention and, of course, should not be construed as in any way limiting its scope.

EXAMPLE 1

This example describes the synthesis of DEA/NO $((C_2H_5)_2N[N(O)NO]^-Na^+)$ and assay of DEA/NO for nitric oxide (NO) production.

DEA/NO was synthesized from sodium nitrite and diethylamine (both from Aldrich, Milwaukee, Wis.) and assayed for NO production using chemiluminescence as described by Maragos et al. (1991), supra. Stock solutions of DEA/NO (Chemical Abstracts Service Registry Number 86831-65-4) were made up in 0.02N NaOH, and the concentrations of the stock solutions were confirmed spectrophotometrically, using an extinction coefficient of $8 \times 10^3$ $M^{-1}cm^{-1}$ at 247 nm.

EXAMPLE 2

This example describes the culture of Chinese hamster V79 lung fibroblasts.

Chinese hamster V79 lung fibroblasts were cultured in F12 medium supplemented with 10% fetal calf serum and antibiotics. Cell survival under aerobic and hypoxic conditions was assessed by in vitro clonogenic assay with plating efficiency ranging between 70–90% (Ham and Puck, *Enzymologia*, 5, 90–119 (1962); Puck and Markus, *J. Exp. Med.*, 103, 653–666 (1956)). The assay system was specifically designed to evaluate radiation sensitivity of cells exposed to radiation under both aerobic and hypoxic conditions (Mitchell et al., *Radiat. Res.*, 96, 422–428 (1983); Russo et al., *Radiat. Res.*, 103, 232–239 (1985); and DeGraff et al., *Int. J. Radiat. Oncol. Biol. Phys.*, 16, 1021–1024 (1989)).

When cultured cells were exposed to DEA/NO in subsequent examples, DEA/NO in F12 medium with 10 mM HEPES buffer, pH 7.0, was used. DEA/NO addition to F12 medium resulted in a final pH of 7.1–7.3. Control cells in subsequent examples were exposed to 0.02N NaOH, instead of DEA/NO.

EXAMPLE 3

This example describes the use of metabolism mediated oxygen depletion in dense cell suspensions to generate hypoxic Chinese hamster V79 lung fibroblasts for DEA/NO studies.

The induction of hypoxia in dense cell suspensions by metabolism-mediated oxygen depletion was carried out as described by Mitchell et al. (supra) and Phillips et al. (*Int. J. Radiat. Oncol. Biol. Phys.*, 12, 1627–1635 (1986)). Briefly, stock cultures of exponentially growing Chinese hamster V79 lung fibroblasts in 850 cm² roller bottles were trypsinized, rinsed with medium, and counted. Samples of $10^8$ cells were then placed in 15 ml centrifuge tubes, centrifuged at 1,000 rpm for 5 min at 25° C., and rinsed once with medium or medium containing DEA/NO (final concentrations ranging from 0.1–2.0 mM), nitrite, diethylamine, or DEA/NO that had been allowed to decompose in full medium overnight at 37° C.

The cell pellet, which ranged in volume from 0.15–0.25 ml of packed cells, was then resuspended to $10^8$ cells/ml in complete medium containing 10 mM HEPES with or without the drugs cited above. The cell suspension was taken up into a 3 ml glass syringe with a 18 gauge spinal needle. Air bubbles were removed, and a 25 gauge needle was fitted onto the syringe. The syringe was rotated by hand at room temperature for 20 min to allow for cellular metabolic oxygen consumption. The syringe was then placed in a lucite block and irradiated. After a given dose of radiation, 1–3 drops of cell suspension were discarded, and 1–2 drops were collected in tubes containing drug-free medium. In this manner an entire hypoxic survival curve for a given treatment condition can be obtained from a single syringe.

EXAMPLE 4

This example describes a method of inducing hypoxia by plating cells into glass flasks and gassing the resulting cell monolayer with nitrogen to produce hypoxic Chinese hamster V79 lung fibroblasts for NO gas studies.

Chinese hamster V79 lung fibroblasts from exponentially growing stock cultures were plated into specially designed 25 cm² glass flasks ($2.5\times10^5$ cells in 2 ml of medium/flask) (Russo et al., supra) and incubated at 37° C. overnight. Two 19 gauge needles were pushed through a rubber stopper inserted into each flask to provide entrance and exit ports for a humidified gas mixture of 95% nitrogen/5% $CO_2$ (Matheson Gas Products, Rutherford, N.J.). Stoppered flasks were connected in series and mounted on a reciprocating platform and gassed at 37° C. for 45 minutes. The gassing procedure resulted in an equilibrium between the gas and liquid phases and yielded oxygen concentrations in the effluent gas phase of <10 ppm as measured by a Thermox probe (Russo et al., supra). After 45 min of deoxygenating, flasks were disconnected from the gassing system, leaving a slightly positive pressure of the $N_2/CO_2$ atmosphere within the flask. Once flasks are disconnected from the gassing system, radiobiological hypoxic conditions can be maintained for several hours (Russo et al., supra).

Various partial pressures of NO in the head space above the cell monolayer were achieved by the following method. The head space volume in the flask above the cell monolayer was determined by weighing the amount of water to fill the flask and subtracting the volume of medium present during gassing (2.0 ml). Specific volumes of NO were delivered by means of an airtight syringe containing a teflon-tipped plunger to the headspace to achieve the desired partial pressures of NO ranging from $2.5\times10^3$ to $10^5$ ppm. After NO gas injection, the flasks were gently rocked for 10 min to facilitate equilibrium of NO with the medium and then irradiated. After irradiation, the stoppers were quickly removed, and the cell monolayer was immediately gassed with 95% $N_2$ for 2 min. This precaution was taken to prevent the reaction of NO in the gas phase with oxygen, which can form potentially cytotoxic $NO_x$ species and produce conditions of extreme acidic pH. After gassing, the cell monolayer was rinsed, trypsinized, counted, and plated for macroscopic colony formation as described below.

EXAMPLE 5

This example describes the irradiation of hypoxic Chinese hamster V79 fibroblasts.

Hypoxic Chinese hamster V79 lung fibroblasts of Example 2 were irradiated at room temperature with 4 MeV photons from a linear accelerator at a dose rate of 1.5 Gy/min. Full electron equilibrium was ensured for all irradiations.

Following irradiation, the various cell suspensions were pipetted, counted, diluted, and plated for macroscopic colony formation. Each dose determination was plated in triplicate and experiments were repeated a minimum of two times. Plates were incubated for seven days, after which colonies were fixed with methanol/acetic acid (3:1), stained with crystal violet, and counted. Colonies containing >50 cells were scored and graphed as FIGS. 1–3. Error bars in the graphs represent the standard deviation of the mean and are shown when larger than the symbol used to designate a data point. Survival curve data were fitted using a linear quadratic model of Albright (Radiat. Res., 112, 331–340 (1987)), and the survival curves shown in the figures represent the best fit curves for the experimental data points. Sensitizer enhancement ratios (SER) were calculated by dividing the radiation dose for control hypoxic conditions by the radiation dose for various agents under hypoxic conditions at the 1% surviving fraction level. An SER of 1.0 indicates that the agent did not sensitize hypoxic cells to radiation, whereas an SER of 3.0 indicates that the agent eliminated hypoxic cell resistance to radiation, i.e., that the agent rendered the hypoxic cells susceptible to radiation.

Control aerobic irradiations were carried out at a lower cell density ($3\times10^5$/ml) in 5 ml plastic dilution tubes. To minimize air space above the cell suspensions, which might allow NO released for DEA/NO to escape from the solution, the dilution tubes were filled to the top with cell suspensions, with or without drug, and capped. Various concentrations (final concentrations ranging from 0.1 to 2.0 mM) of DEA/NO, nitrite, diethylamine, or DEA/NO allowed to decompose in full medium overnight at 37° C. were added to the cell suspensions 20 min prior to radiation exposure. The tubes were placed in the lucite block and irradiated, and, following irradiation, the cell suspensions were rinsed and processed for survival as described above.

Radiation survival curves for V79 cells exposed to varying concentrations of DEA/NO and various DEA/NO decomposition products under hypoxic conditions (metabolic hypoxia induction) are shown in FIG. 1A, which is a graph of the surviving fraction versus dose (Gy). Lines in FIG. 1A represent control (●) and 0.1 mM (Δ), 0.5 mM (○), 1.0 mM (□), and 2.0 mM (■) DEA/NO. Survival curves were corrected for drug cytotoxicity as appropriate. DEA/NO treatment alone was not cytotoxic for concentrations ranging from 0.1–1.0 mM and resulted in minimal cytotoxicity at 2 mM (70%). FIG. 1A and Table I below show that DEA/NO treatment resulted in concentration-dependent radiosensitization of hypoxic V79 cells. While the extent of radiosensitization was modest for 0.1 mM DEA/NO, significant enhancement was observed for the 0.5 and 1.0 mM treatments. Increasing the DEA/NO concentration to 2.0 mM resulted in a SER of 2.9±0.4, indicating that, at this concentration, DEA/NO is just as effective as oxygen in eliminating radiation resistance due to hypoxia. It should be noted that the radiosensitization achieved with NONOates is significantly greater than that achieved with 1 mM nitroimidazole, which suffers from other shortcomings as noted above (Adams et al. (1976), supra).

Figure 1B:
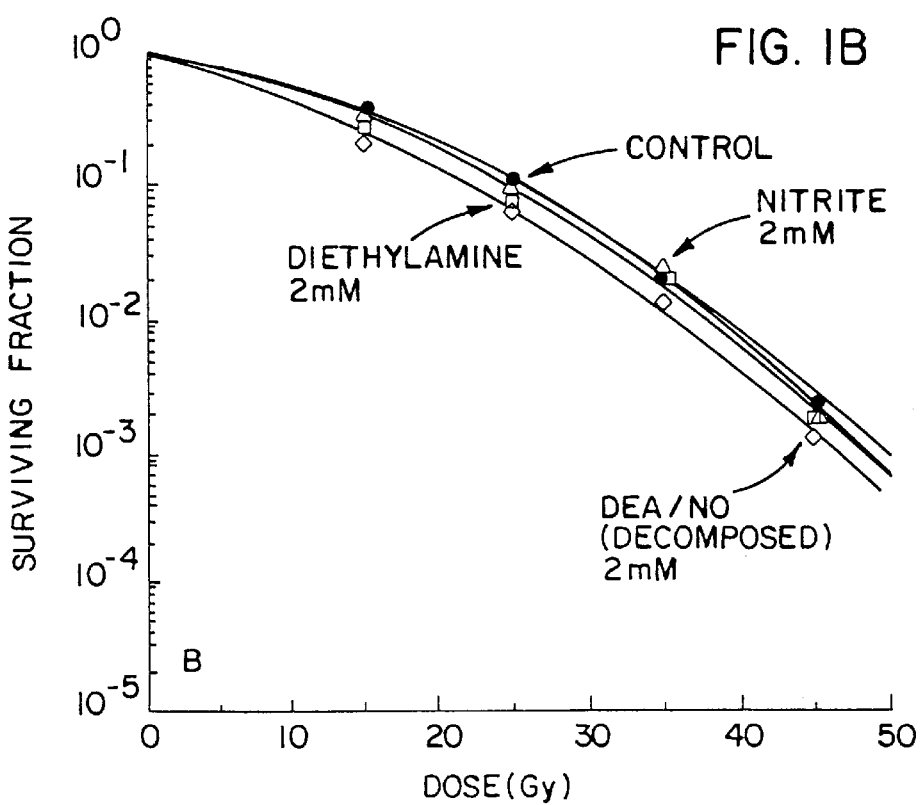

Control experiments, which evaluated the decomposition products of DEA/NO, nitrite, and diethylamine, were conducted to determine if the radiation sensitization observed was due to the NO liberated from DEA/NO and present at the time of irradiation. DEA/NO (2.0 mM) was allowed to decompose to liberate NO in medium maintained at 37° C. overnight in a flask open to the air for use as an additional control. The medium containing the DEA/NO decomposition products was then used to evaluate possible effects on radiosensitization. Neither nitrite, diethylamine, or decomposed DEA/NO alone resulted in any cytotoxicity, nor did any of these agents significantly modify hypoxic radiosensitivity as shown in FIG. 1B, which is a graph of surviving fraction versus dose (Gy) under aerobic conditions, wherein the lines represent control (●) and 2.0 mM nitrite (Δ), diethylamine (□), and decomposed DEA/NO (◊). Based on these controls, it can be concluded from the studies shown in FIG. 1A and Table I that the hypoxic radiosensitization observed was due to the NO released from DEA/NO and present at the time of irradiation.

TABLE I

SERs for DEA/NO and Related Decomposition products

| Agent | Conc. (mM) | SER (±SD) |
|---|---|---|
| DEA/NO | 0.05 | 1.0 |
| | 0.10 | 1.1 ± 0.06 |
| | 0.50 | 2.1 ± 0.40 |
| | 1.00 | 2.4 |
| | 2.00 | 2.9 ± 0.40 |
| Nitrite | 2.00 | 1.0 |
| Diethylamine | 2.00 | 1.0 |
| DEA/NO (Decomposed) | 2.00 | 1.0 |

NOTE: The OER for this hypoxic system was 2.8 ± 0.4

Figure 2A:
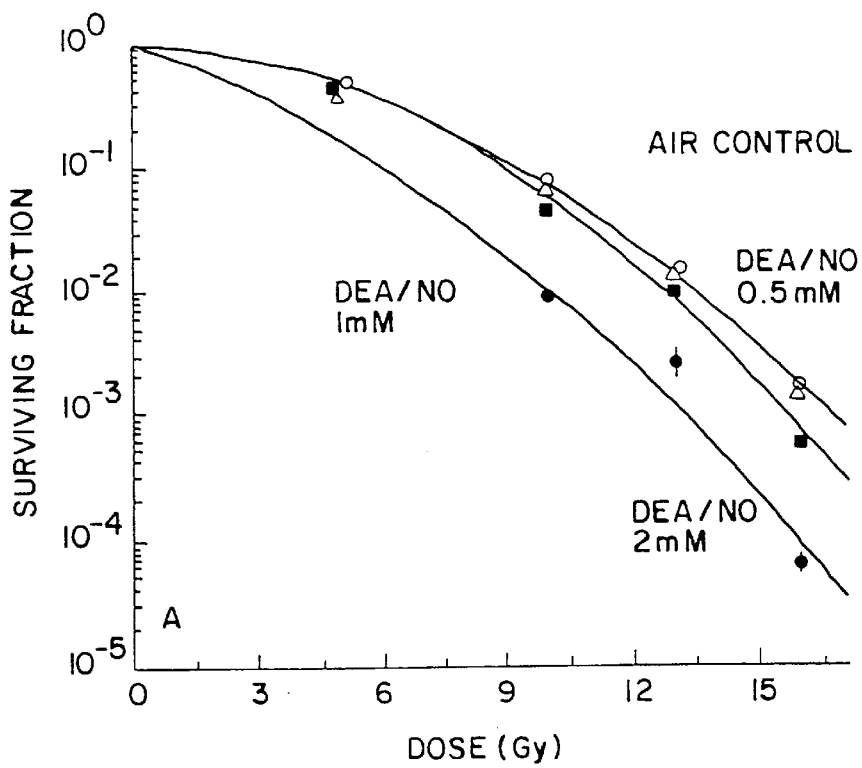
FIGS. 2A and 2B are graphs of surviving fraction versus radiation dose (Gy) showing the radiation survival curves for V79 fibroblasts exposed to various concentrations of DEA/NO (FIG. 2A) or nitrite, diethylamine, or DEA/NO decomposition products (FIG. 2B) under aerobic conditions.
Figure 2B:
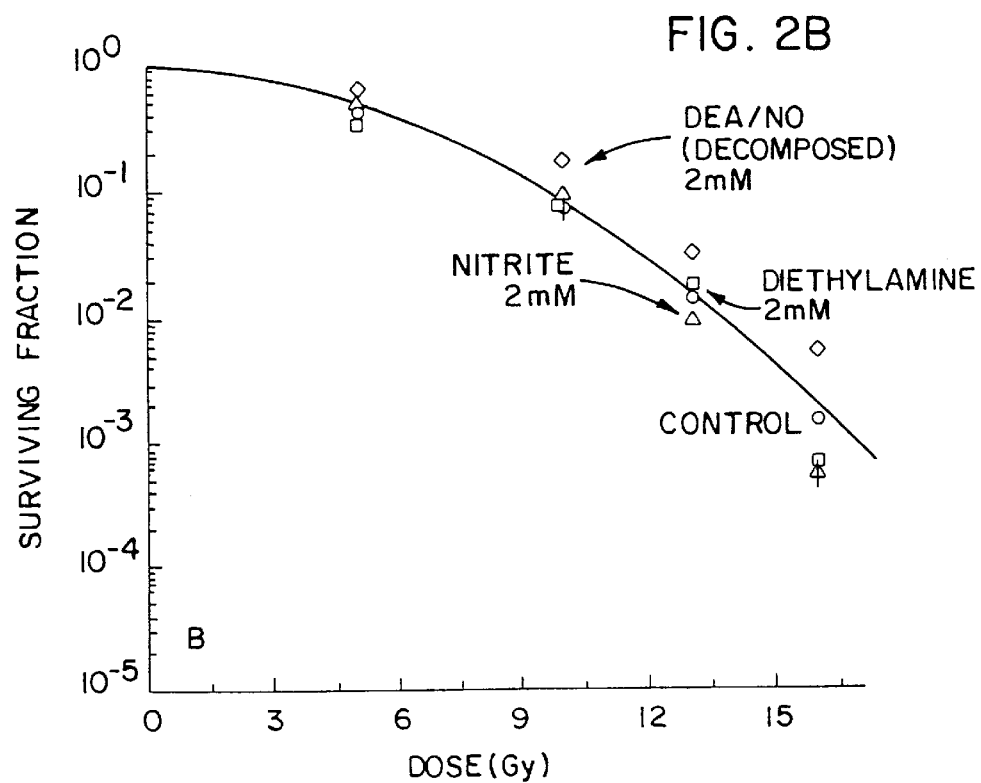
Figure 3A:
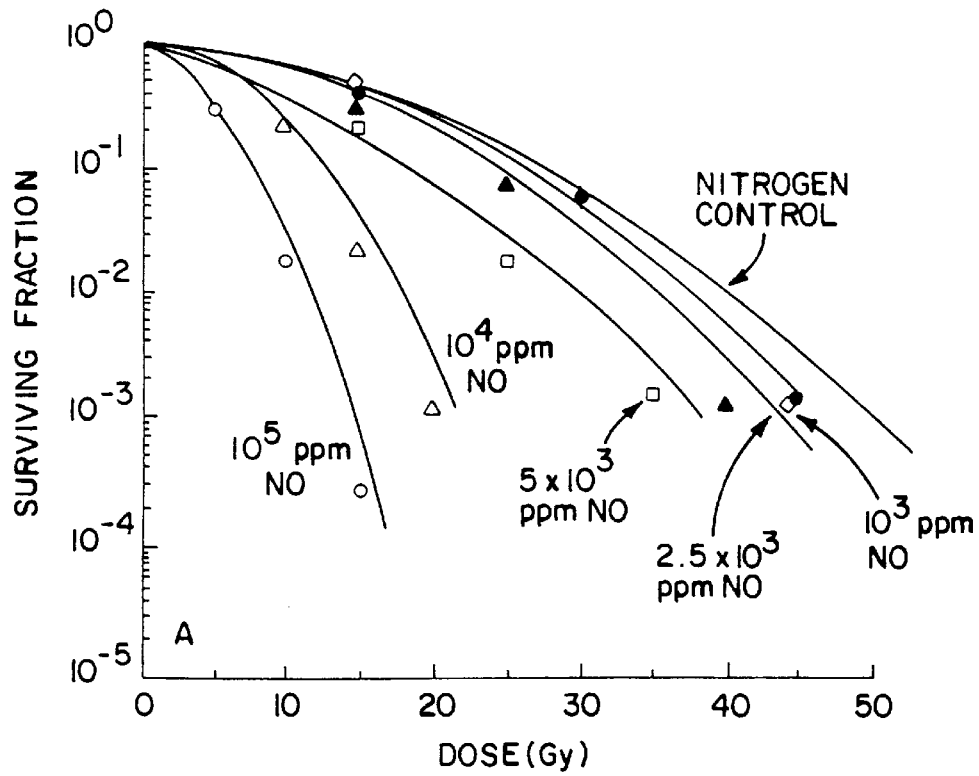
FIG. 3A is a graph of surviving fraction versus radiation dose (Gy) showing the radiation survival curves for V79 fibroblasts exposed to varying concentrations of NO gas under hypoxic conditions.
Figure 3B:
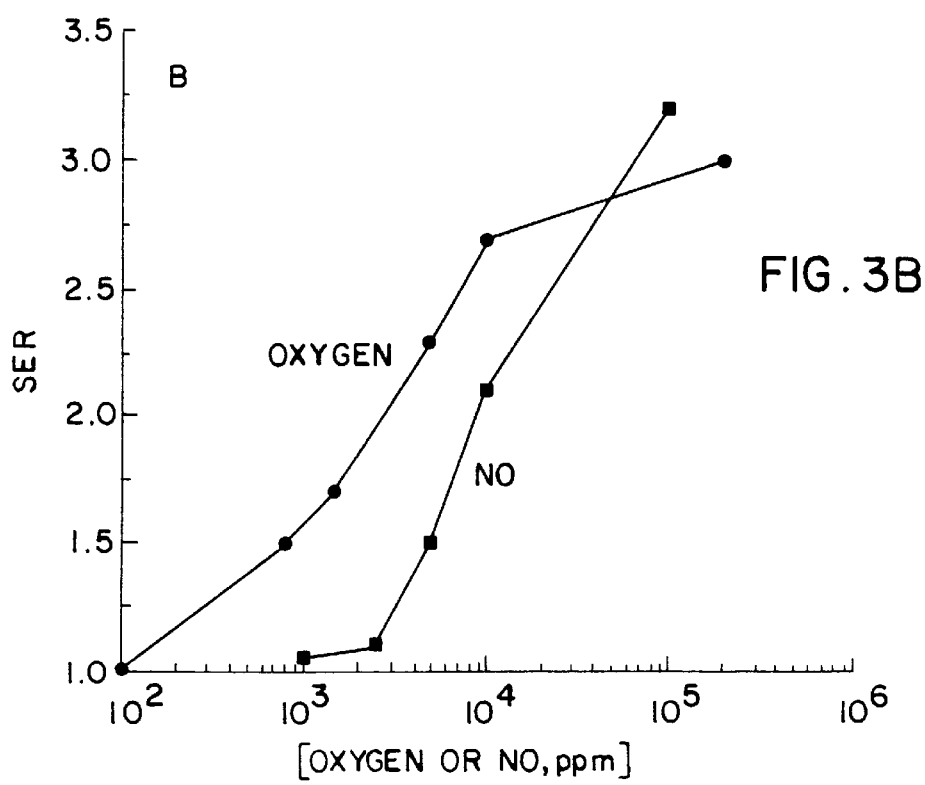
FIG. 3B is a graph of the sensitizer enhancement ratio (SER) as a function of oxygen or NO concentration (ppm).

The effects of DEA/NO on aerobic radiosensitivity is shown in the radiation survival curve for V79 cells exposed to varying concentrations of DEA/NO or DEA/NO decomposition products under aerobic conditions in FIG. 2A, which is a graph of surviving fraction versus dose (Gy), wherein the lines represent control (○) and 0.5 mM (△), 1.0 mM (■), and 2.0 mM (●) DEA/NO. DEA/NO concentrations of 0.5 and 1.0 mM had no effect on aerobic radiosensitivity; however, 2.0 mM DEA/NO enhanced aerobic radiosensitivity (enhancement at the 1% survival level was 1.3). Controls similar to those described above also were performed under aerobic conditions and are shown in the radiation survival curve for V79 cells exposed to varying concentrations of DEA/NO or DEA/NO decomposition products under aerobic conditions as shown in FIG. 2B, which is a graph of surviving fraction versus dose (Gy), wherein the lines represent control (○) and 2.0 mM nitrite (△), diethylamine (□), and decomposed DEA/NO (◊). Nitrite, diethylamine, and decomposed DEA/NO did not significantly alter the aerobic radiosensitivity of V79 cells.

EXAMPLE 6

This example describes the verification that NO is a hypoxic radiosensitizer for mammalian cells.

Chinese hamster V79 lung fibroblasts were grown as monolayers in glass flasks and were first gassed with nitrogen, and then known amounts of NO gas were injected into the sealed flask to yield final concentrations ranging from $10^3$–$10^5$ ppm NO at the time of irradiation. NO gas was found to be a potent hypoxic cell radiosensitizer as shown in the radiation survival curve for V79 cells exposed to varying concentrations of NO gas under hypoxic conditions in FIG. 3A, which is a graph of surviving fraction versus dose (Gy), wherein the lines represent control (●), 1000 ppm NO (◊), $2.5\times10^3$ ppm NO (▲), $5\times10^3$ ppm NO (□), $10^4$ ppm NO (△), and $10^5$ ppm NO (○). NO gas treatment resulted in a concentration-dependent enhancement of hypoxic radiosensitivity with the highest concentration ($10^5$ ppm) yielding a SER of 3.2. The radiosensitization of hypoxic V79 cells by NO is compared to that for oxygen in FIG. 3B, which is a graph of the sensitizer enhancement ratio (SER) as a function of oxygen (●) or NO (■) concentration (ppm). The response curve was generated as described by Russo et al. (supra). NO gas was not as efficient as oxygen in hypoxic cell radiosensitization, yielding a k value (concentration required to yield half the maximum effect) of $10^4$ ppm compared to $2.5\times10^3$ ppm for oxygen.

EXAMPLE 7

This example demonstrates that nitric oxide-releasing compounds, such as SPER/NO and SNAP, sensitize hypoxic cells to radiation in vitro.

Figure 5:
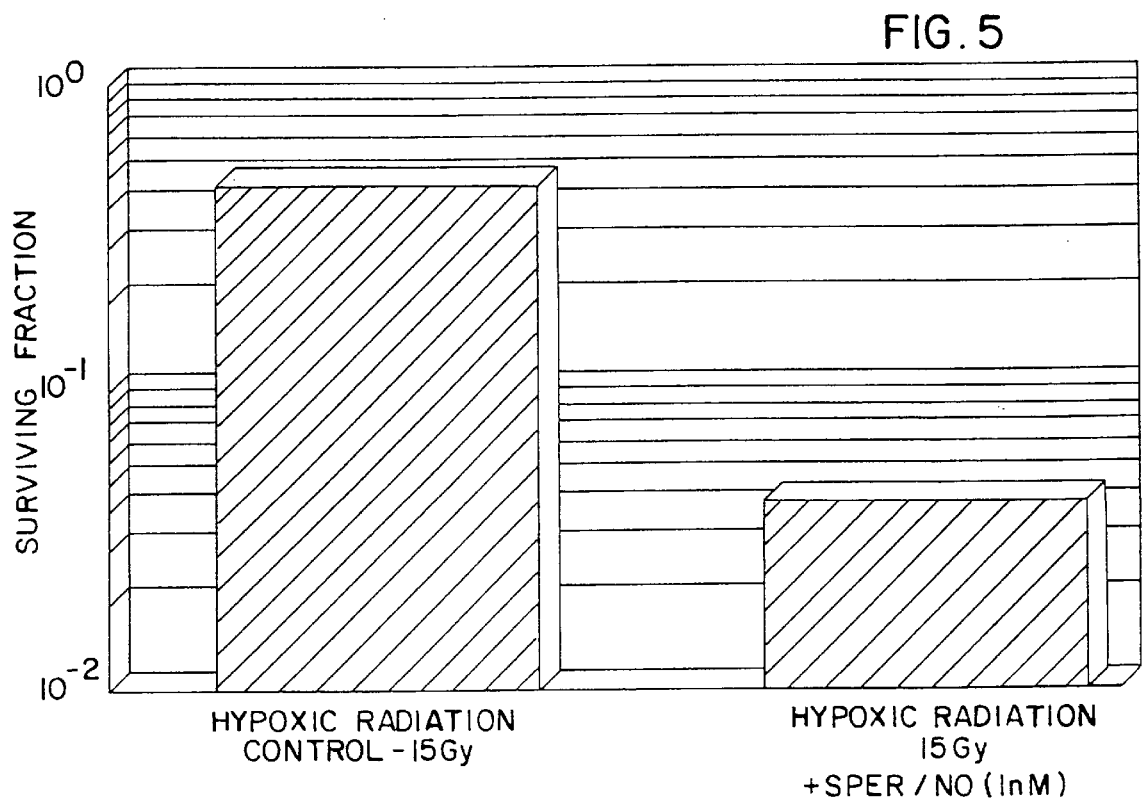
FIG. 5 is a bar graph of surviving fraction versus tumors treated under hypoxic conditions with 15 Gy radiation or SPER/NO followed by 15 Gy radiation.

Chinese hamster V79 cells were exposed to 15 Gy radiation under hypoxic conditions in the absence or presence of 1 mM SPER/NO ($H_2N(CH_2)_3N[N(O)NO]^-(CH_2)_4NH_2^+$ $(CH_2)_3NH_2$). SPER/NO-treated hypoxic cells were more susceptible to radiation than control cells as shown in FIG. 5, which is a bar graph of surviving fraction versus the test groups of Control (15 Gy radiation dose) and SPER/NO (1 mM plus 15 Gy radiation dose).

Figure 6:
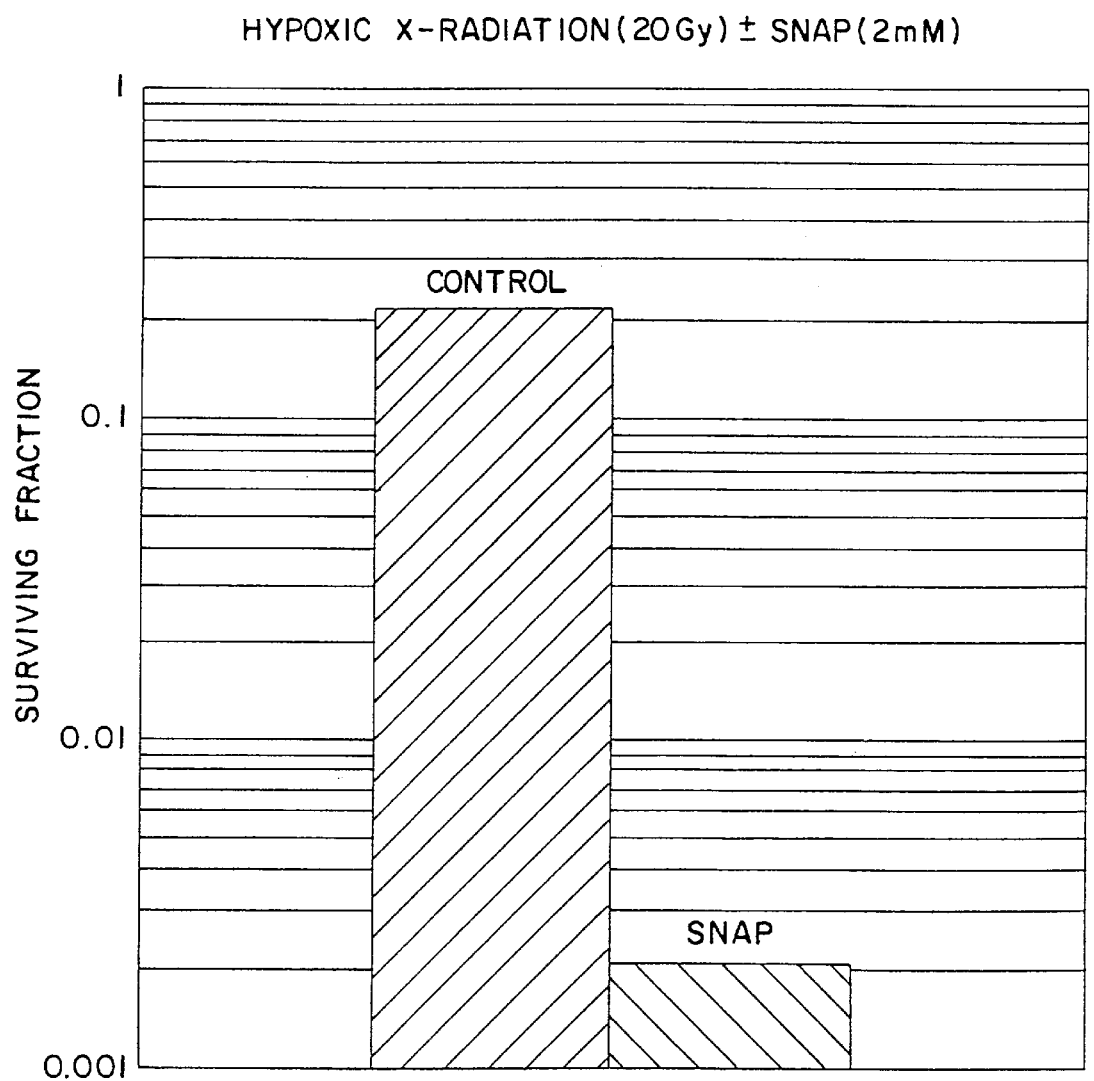
FIG. 6 is a bar graph of surviving fraction versus tumors treated under hypoxic conditions with 20 Gy radiation in the presence or absence of 2 mM SNAP.

Chinese hamster V79 cells were exposed to 20 Gy radiation under hypoxic conditions in the absence or presence of 2 mM SNAP. SNAP-treated hypoxic cells were significantly more susceptible to radiation than control cells as shown in FIG. 6, which is a bar graph of surviving fraction versus the test groups of Control (20 Gy radiation dose) and SNAP (2 mM plus 20 Gy radiation dose).

EXAMPLE 8

This example demonstrates that the nitric oxide-releasing compound GSNO sensitizes hypoxic cells to radiation in vitro.

Figure 8:
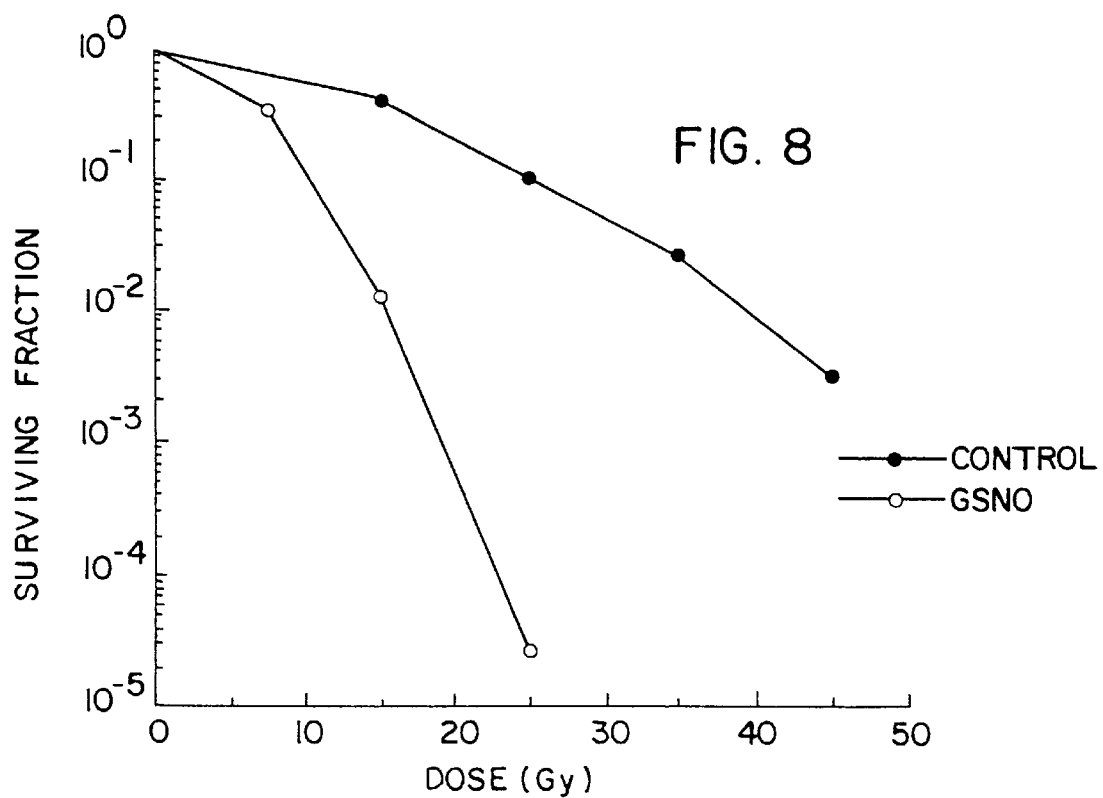
FIG. 8 is a graph of surviving fraction versus radiation dose (Gy) showing the radiation survival curves for V79 cells exposed to radiation under hypoxic conditions in the absence or presence of 1 mM GSNO.

Chinese hamster V79 cells were exposed to radiation under hypoxic conditions in the absence or presence of 1 mM GSNO. GSNO-treated hypoxic cells were more susceptible to radiation than control cells as shown in FIG. 8, which is a graph of surviving cell fraction versus radiation dose (Gy) showing the radiation survival for V79 cells exposed to radiation under hypoxic conditions in the absence or presence of 1 mM GSNO. GSNO treatment yielded a SER of 2.7 at the 1% surviving fraction level, which is comparable to DEA/NO (SER=2.4 at 1 mM, Table I).

EXAMPLE 9

This example demonstrates that nitric oxide-releasing compounds, such as DEA/NO, sensitize hypoxic cells to radiation in vivo.

A murine tumor model (KHT) known to have a hypoxic component (Siemann et al., *Br. J. Cancer*, 58, 296–300 (1988)) was used to show that NONOates sensitize hypoxic tumor cells to radiation in vivo. This murine model is one which is routinely used to test hypoxic radiosensitizers. In fact, results obtained with this model were used as a basis for initiating clinical trials of nitroimidazoles as radiation sensitizers in the early to mid-1970's.

Figure 4:
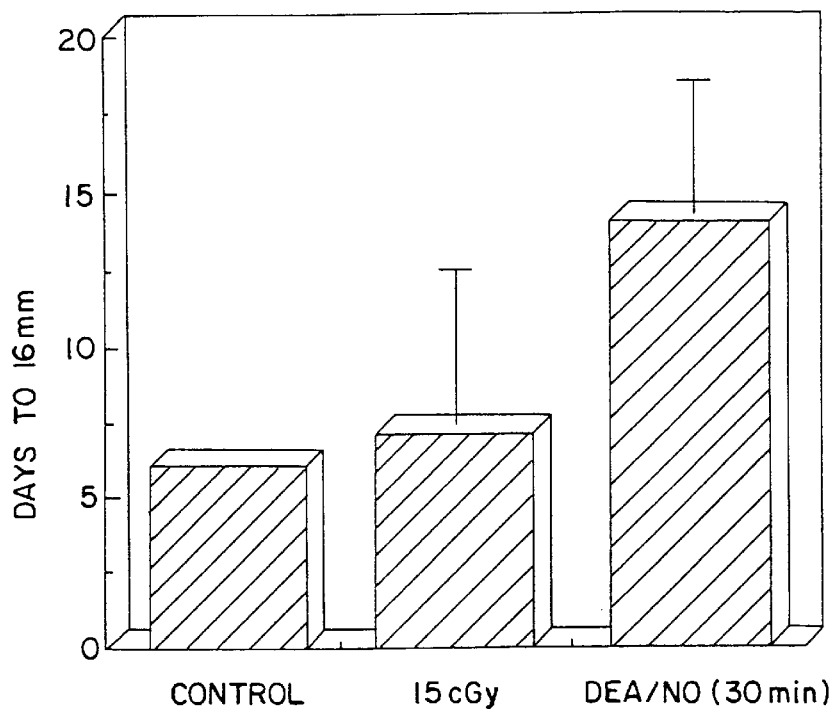
FIG. 4 is a bar graph of the number of days required for tumors to regrow to 16 mm in diameter versus tumors treated with DEA/NO alone (Control), 15 cGy radiation, and DEA/NO followed by 15 cGy radiation 30 minutes later.

C3H mice with hind leg implants of KHT tumors were exposed to radiation. When the tumors had grown to 8 mm in circumference, the mice were treated with DEA/NO alone (control), 15 cGy directed at the tumor, or DEA/NO given 30 minutes before tumor irradiation with 15 cGy (DEA/NO (30 min)). The mice experienced a tumor regrowth delay of one day after treatment of the tumor with 15 cGy. Mice pretreated with DEA/NO (80 mg/kg) 30 min before tumor irradiation demonstrated a tumor regrowth delay of 8 days. In DEA/NO-treated mice, 14% of tumors were eradicated by 15 cGy, whereas control mice did not demonstrate any tumor cures. Two animals in the DEA/NO (30 min) group survived for at least four weeks with no evidence of tumor. These results are summarized in FIG. 4, which is a bar graph of the number of days required for a tumor to reach 16 mm in diameter versus the test groups of Control (n=15), 15 cGy (n=15), and DEA/NO (30 min; n=14).

EXAMPLE 10

This example demonstrates that the putative NO-releasing agent 3-morpholino-sydnonimine hydrochloride (SIN-1) does not sensitize hypoxic cells to radiation in vitro.

Figure 9:
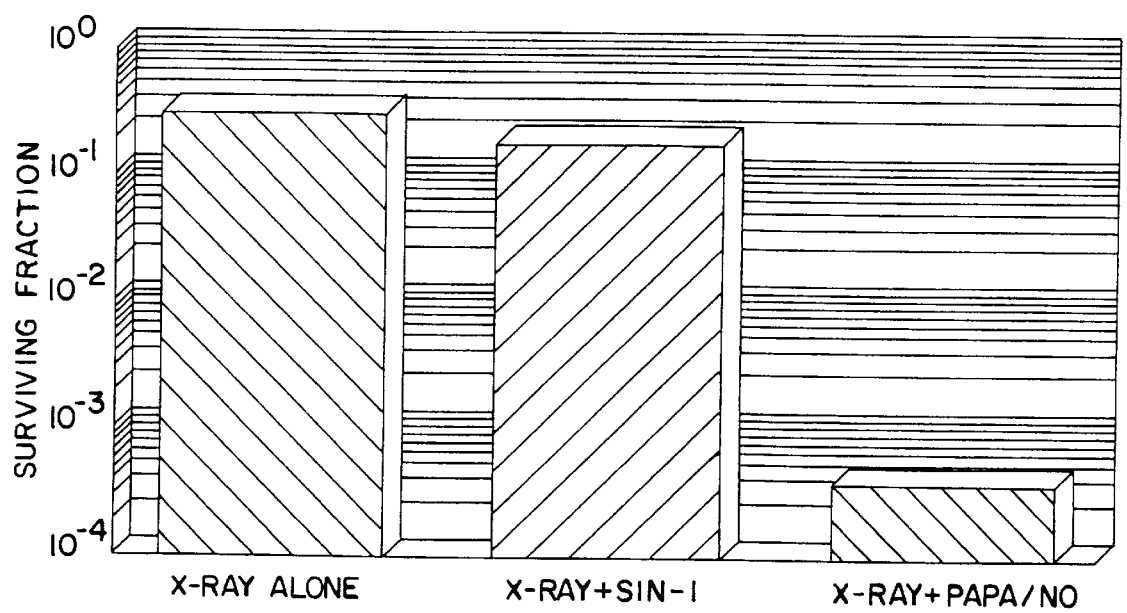
FIG. 9 is a bar graph of surviving fraction versus V79 cells exposed to 20 Gy radiation under hypoxic conditions in the presence or absence of 2 mM SIN-1 or PAPA/NO.

Chinese hamster V79 cells were exposed to a single 20 Gy dose of radiation in the absence or presence of 2 mM SIN-1 or PAPA/NO. PAPA/NO-treated hypoxic cells were much more susceptible to radiation than control cells, whereas SIN-1-treated cells were not significantly sensitized to radiation as compared to control cells as shown in FIG. 9, which is a bar graph of surviving fraction versus the test groups of Control (X-ray alone), SIN-1 (X-ray+SIN-1) and PAPA/NO (X-ray+PAPA/NO). The data are consistent with the requirement of SIN-1 for oxygen, unlike the NONOates, which release NO independent of oxygen levels. Accordingly, agents like the NONOates are superior compared to agents like SIN-1 in sensitizing hypoxic cells to radiation.

EXAMPLE 11

This example demonstrates that nitric oxide-releasing compounds, such as DEA/NO, protect noncancerous cells and tissues from radiation in vivo.

Female C3H mice were obtained from the Frederick Cancer Research Center—Animal Production in Frederick, Md. C3H mice have been used in whole body irradiation studies since 1948 (Patt, et al., *Science*, 110, 213–214 (1949)) and are considered to serve as good models for predicting the effects of radiation in humans.

C3H mice were received at six weeks of age and were housed five per cage in climate-controlled, circadian rhythm-adjusted rooms and allowed food and water ad libitum. The animals were 60–80 days old at the time of radiation. A total of 10–15 mice were used per radiation dose. Mice were weighed in groups of five. The weights of each group ranged from 110 grams to 135 grams or an average weight of 22–27 grams per mouse.

In all experiments drugs and diluent (in control mice) were injected intraperitoneally into mice in volumes equivalent to 1% of each animal's weight (0.22 to 0.27 ml). Groups of 5–10 mice were placed in round (30.5 cm diameter and 10.5 cm height) Plexiglas containers with holes for ventilation for irradiation. The irradiator was calibrated with thermoluminescent dosimetry chips planted in phantom mice, and the radiation dose was determined according to previously described methodology (Cameron et al., "Thermoluminescent Dosimetry" (Univ. of Wisconsin Press, Madison, Wis., 1968)). The dose rate used was 1 Gy/min. Total time of irradiation varied as a function of the dose delivered. Immediately after irradiation, the mice were separated into groups of five and returned to climate-controlled cages for observation. The mice were assessed daily for survival.

Figure 7:
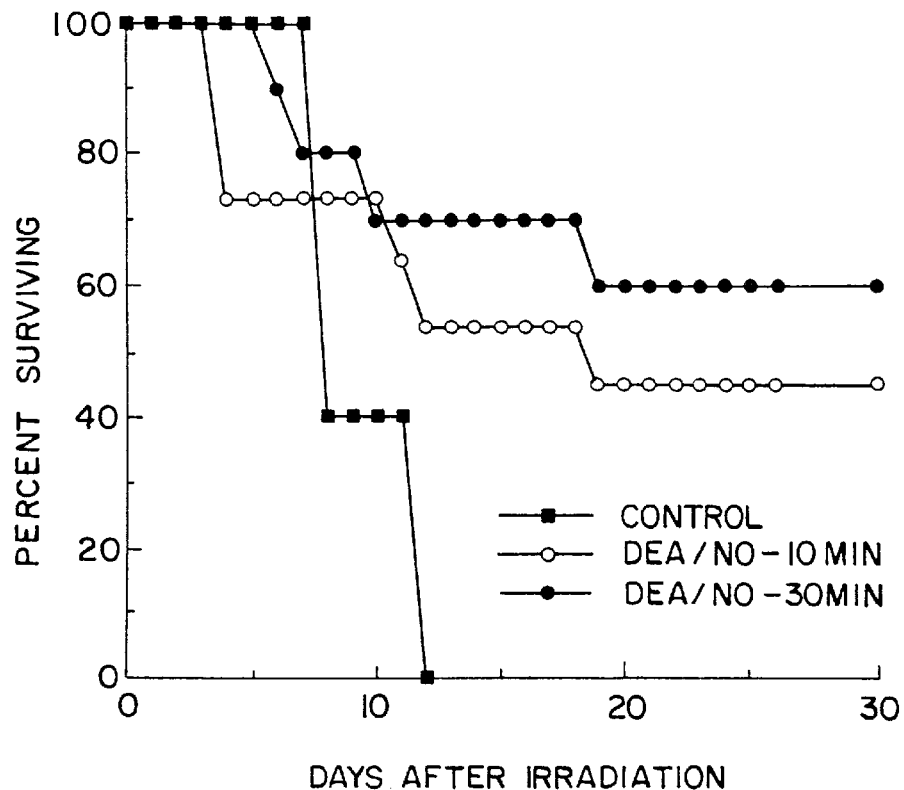
FIG. 7 is a graph of percent surviving versus days after irradiation showing the radiation survival curves for mice exposed to radiation with and without pretreatment with DEA/NO.

Treatment with DEA/NO (80 mg/kg, injected intraperitoneally) between 10 and 30 minutes prior to irradiation protected mice from whole-body irradiation. The results are shown in FIG. 7, which is a graph of percent surviving versus days after irradiation with 11 Gy for control mice (■, n=10), which were injected with saline, mice treated with DEA/NO 10 minutes prior to irradiation (○, n=15), and mice treated with DEA/NO 30 minutes prior to irradiation (●, n=15). FIG. 6 shows the time course of animal survival after whole body irradiation for the first 30 days. Survival at 30 days after irradiation with a variety of radiation doses is shown in Table II. The data in Table II also show that "Reacted DEA/NO", i.e., DEA/NO that had been depleted of NO by prolonged storage at pH 7.4 did not protect animals from whole body irradiation.

TABLE II

Percent survival of mice 30 days after various doses of whole body irradiation

| Radiation (Dose in cGy) | Control (saline) | "Reacted"* DEA/NO | DEA/NO (10 min) | DEA/NO (30 min) |
| --- | --- | --- | --- | --- |
| 700 | 100 | 100 | 100 | 100 |
| 800 | 70 | 60 | 100 | 90 |
| 900 | 7 | 0 | 77 | 80 |
| 1000 | 7 | 0 | 44 | 10 |
| 1100 | 0 | 0 | 44 | 60 |

*DEA/NO (80 mg/kg) that was maintained at pH 7.4 for 24 hours prior to injection.

EXAMPLE 12

This example demonstrates that nitric oxide-releasing compounds, such as DEA/NO, sensitize cancer cells to chemotherapeutic agents, such as alkylating agents, e.g., melphalan and thiotepa, in vitro.

Human breast cancer cells in log phase were exposed for 1 hr at 37° C. to varying concentrations of melphalan or thiotepa in the absence or presence of 1 mM DEA/NO or released DEA/NO. Released DEA/NO is DEA/NO that had been allowed to decompose overnight, thereby releasing all of its NO and leaving only the parent compound diethylamine and any NO reaction products, and, therefore, it served as an additional control. Cytotoxicity was evaluated using the clonogenic assay of Example 2.

Figure 10:
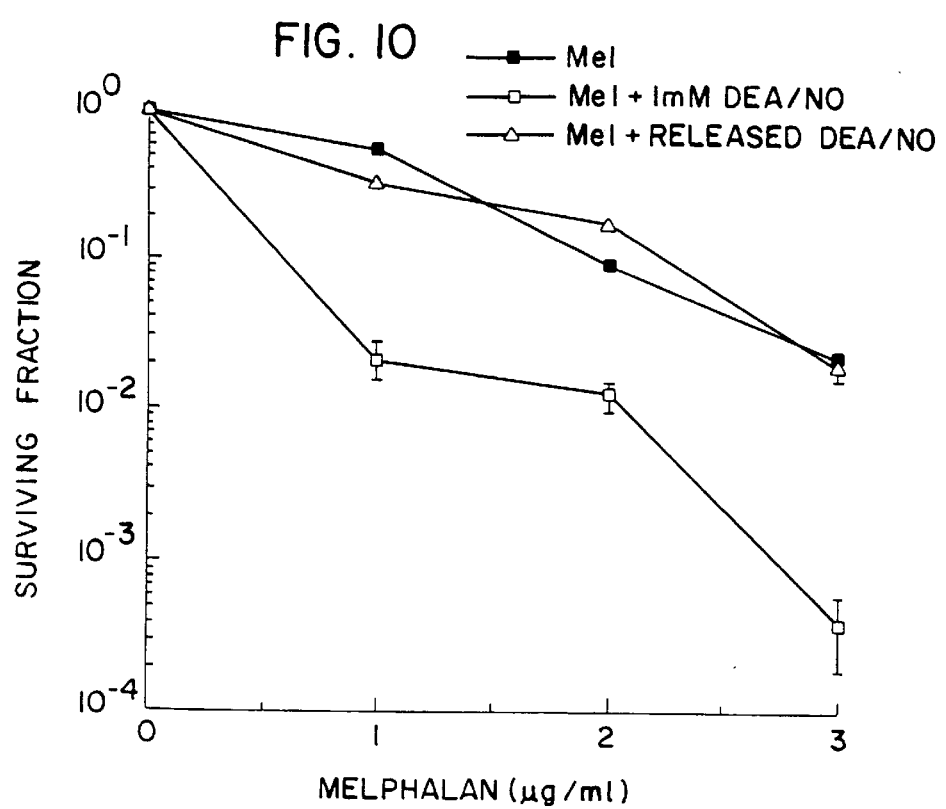
FIG. 10 is a graph of surviving fraction versus concentration (μg/ml) of melphalan in the absence or presence of 1 mM DEA/NO or released DEA/NO showing the survival curves for human MCF7 breast cancer cells exposed to melphalan in the absence or presence of 1 mM DEA/NO or released DEA/NO.
Figure 11:
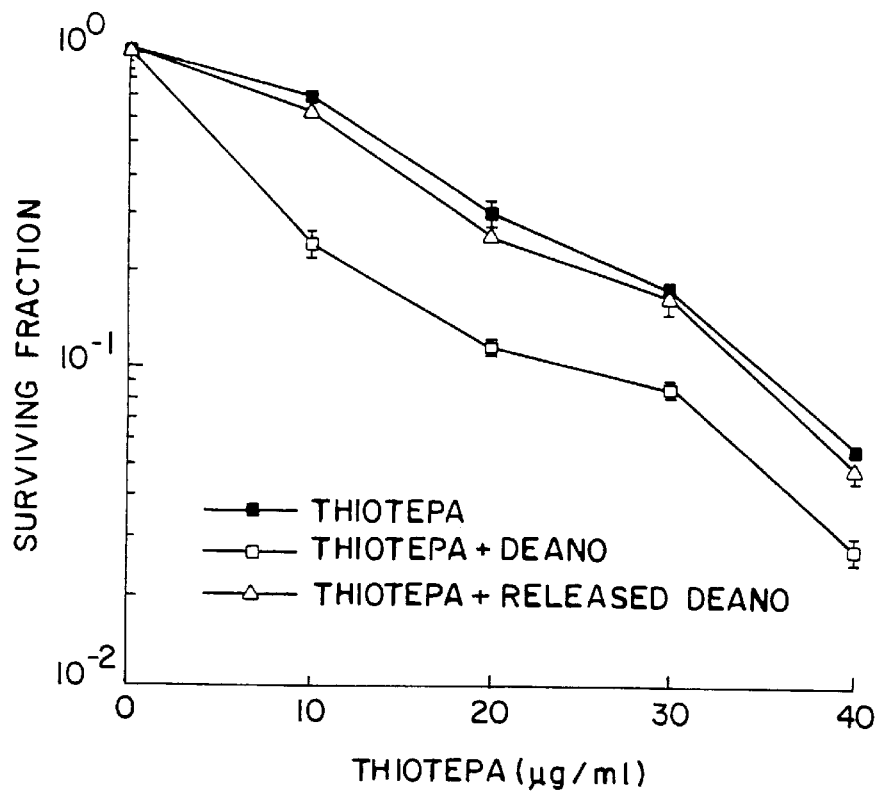
FIG. 11 is a graph of surviving fraction versus concentration (μg/ml) of thiotepa in the absence or presence of 1 mM DEA/NO or released DEA/NO showing the survival curves for human MCF7 breast cancer cells exposed to thiotepa in the absence or presence of 1 mM DEA/NO or released DEA/NO.

FIGS. 10 and 11 are graphs of surviving fraction versus concentration ($\mu$g/ml) of melphalan and thiotepa, respectively. As shown in these figures, DEA/NO significantly enhanced the chemosensitivity of human breast cancer cells to melphalan and thiotepa. In contrast, released DEA/NO did not enhance cytotoxicity. The DEA/NO enhancement ratio (ratio of drug concentration for control cells divided by the drug concentration of DEA/NO-treated cells at the 10% surviving fraction level) was 3.3 for melphalan and 1.3 for thiotepa. Accordingly, these data indicate that the NO released for DEA/NO is capable of enhancing the cytotoxicity of alkylating agents.

EXAMPLE 13

This example demonstrates that nitric oxide-releasing compounds, such as DEA/NO and PAPA/NO, sensitize cancer cells to chemotherapeutic agents, such as bioreductive agents, e.g., mitomycin C and SR 4233, in vitro.

Chinese hamster V79 cells were exposed to varying concentrations of mitomycin C in the absence or presence of 1 mM DEA/NO under aerobic or hypoxic conditions. Aerobic cytotoxicity was evaluated using the clonogenic assay of Example 2, whereas hypoxia cytotoxicity was evaluated using a method similar to that of Example 4.

Figure 12:
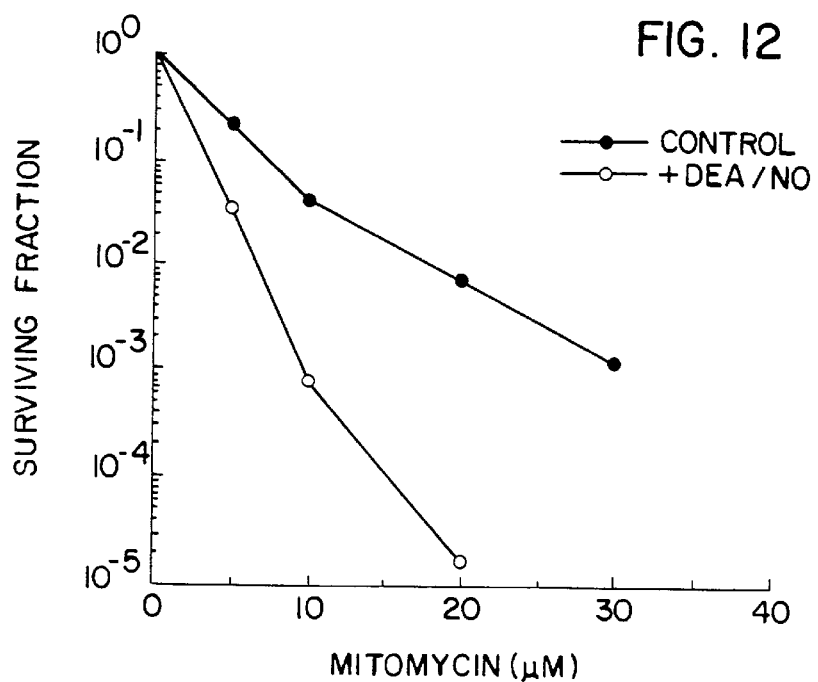
FIG. 12 is a graph of surviving faction versus concentration (μM) of mitomycin C showing the chemotherapy sensitization curves for V79 fibroblasts exposed to varying concentrations of mitomycin C in the absence or presence of DEA/NO under aerobic conditions.
Figure 13:
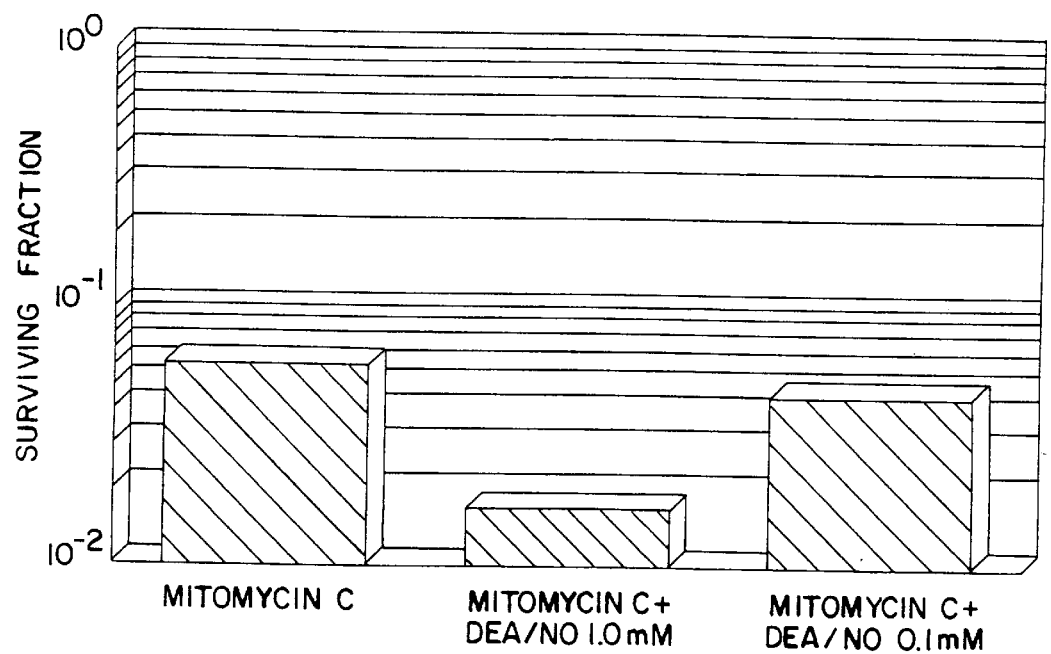
FIG. 13 is a bar graph of surviving fraction versus V79 fibroblasts treated under hypoxic conditions with 5 μM mitomycin C in the absence or presence of 0.1 mM or 1.0 mM DEA/NO.

FIG. 12 is a graph of surviving fraction versus concentration ($\mu$m) of mitomycin C showing the chemotherapy sensitization curves for V79 fibroblasts exposed to varying concentrations of mitomycin C under aerobic conditions. FIG. 13 is a bar graph of surviving fraction versus V79 fibroblasts treated under hypoxia conditions with mitomycin in the absence or presence of 0.1 mm or 1.0 mM DEA/NO. As shown in FIGS. 12 and 13, respectively, DEA/NO enhanced cytotoxicity under both aerobic and hypoxia conditions.

Figure 14:
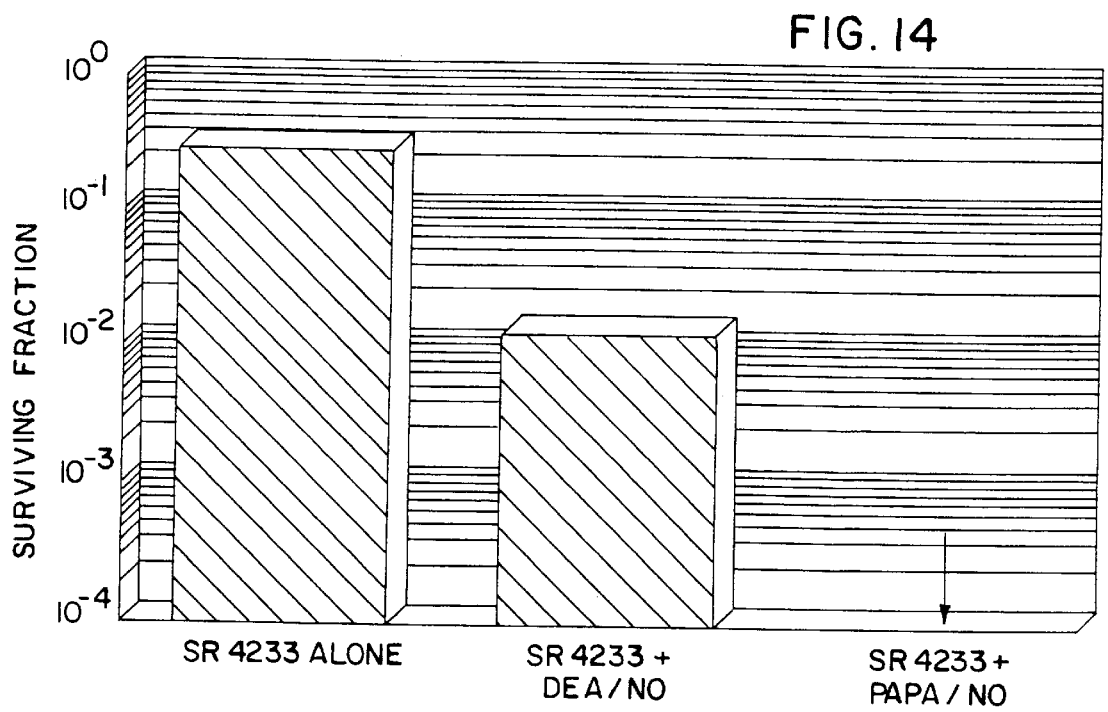
FIG. 14 is a bar graph of surviving fraction versus V79 fibroblasts treated with 25 μM SR 4233 in the absence or presence of 1 mM DEA/NO or PAPA/NO.

Chinese hamster V79 fibroblasts were exposed to 25 $\mu$m SR 4233 in the absence or presence of 1 mM DEA/NO or PAPA/NO under hypoxia conditions for 1 hr. FIG. 14, which is a bar graph of surviving fraction versus V79 fibroblasts treated with 25 μm SR 4233 in the absence or presence of 1 mM DEA/NO or PAPA/NO, shows that DEA/NO and PAPA/NO enhance the hypoxia cytotoxicity of SR 4233. In fact, for PAPA/NO, no colonies were formed when 100,000 cells were plated.

These data show that NO delivered by NONOates enhance the cytotoxicity of bioreductive agents.

EXAMPLE 14

This example demonstrates that nitric oxide-releasing compounds, such as PAPA/NO, can protect cells from chemotherapeutic agents, such as cross-linking agents, e.g., cisplatin, in vitro.

Chinese hamster V79 fibroblasts were exposed to varying concentrations of cisplatin under aerobic conditions for 1 hr in the presence or absence of 1 mM PAPA/NO, n-propyl-1, 3-propane diamine (PPD), or released PAPA/NO under aerobic conditions. Methods used were as described in Examples 2 and 13.

Figure 15:
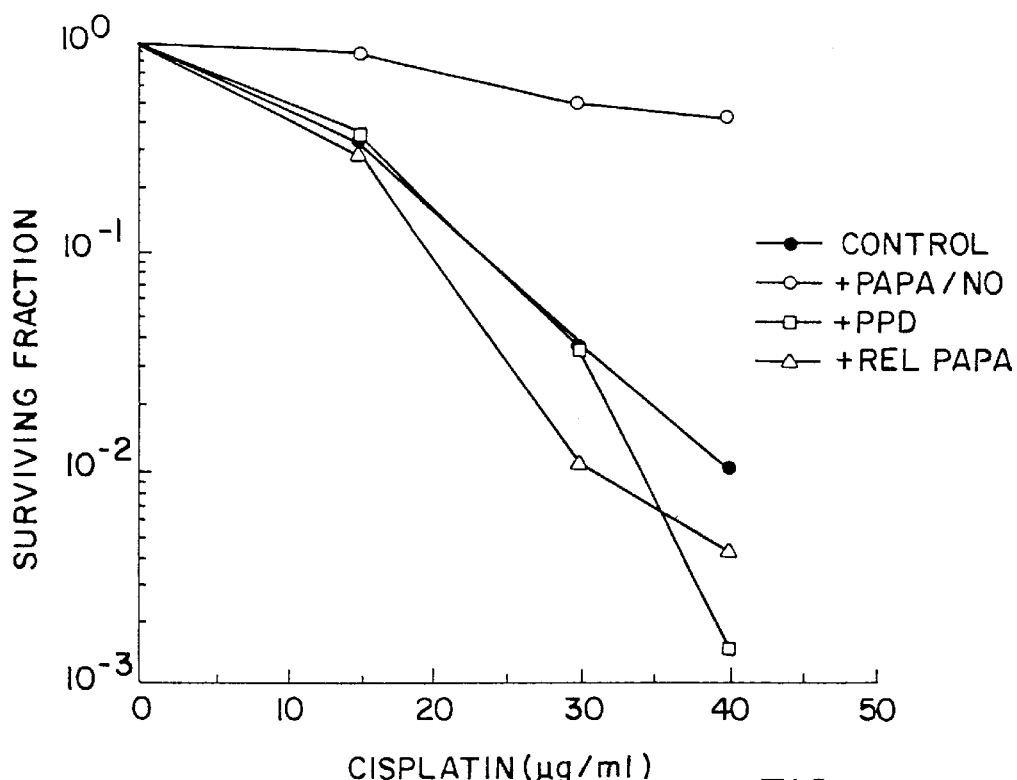
FIG. 15 is a graph of surviving fraction of V79 fibroblasts versus concentration (μg/ml) of cisplatin in the absence or presence of PAPA/NO, n-propyl-1,3-propane diamine (PPD), or 1 mM released PAPA/No, showing the chemotherapy protection curve for V79 fibroblasts treated with cisplatin and PAPA/NO.

FIG. 15 is a graph of surviving fraction versus concentration (μg/ml) of cisplatin in the absence or presence of PAPA/NO, PPD or released PAPA/NO showing the chemotherapy protection curve for V79 fibroblasts. As shown in FIG. 15, PAPA/NO protected V79 fibroblasts against aerobic cisplatin-induced cytotoxicity.

EXAMPLE 15

This example demonstrates that nitric oxide-releasing compounds, such as DEA/NO, can protect against chemotherapy-induced toxicity in vivo.

Female C3H mice were injected intraperitoneally with varying doses of melphalan alone or melphalan with 70 mg/kg DEA/NO. The methods employed were adaptations of the methods used in Examples 9 and 11.

Figure 16:
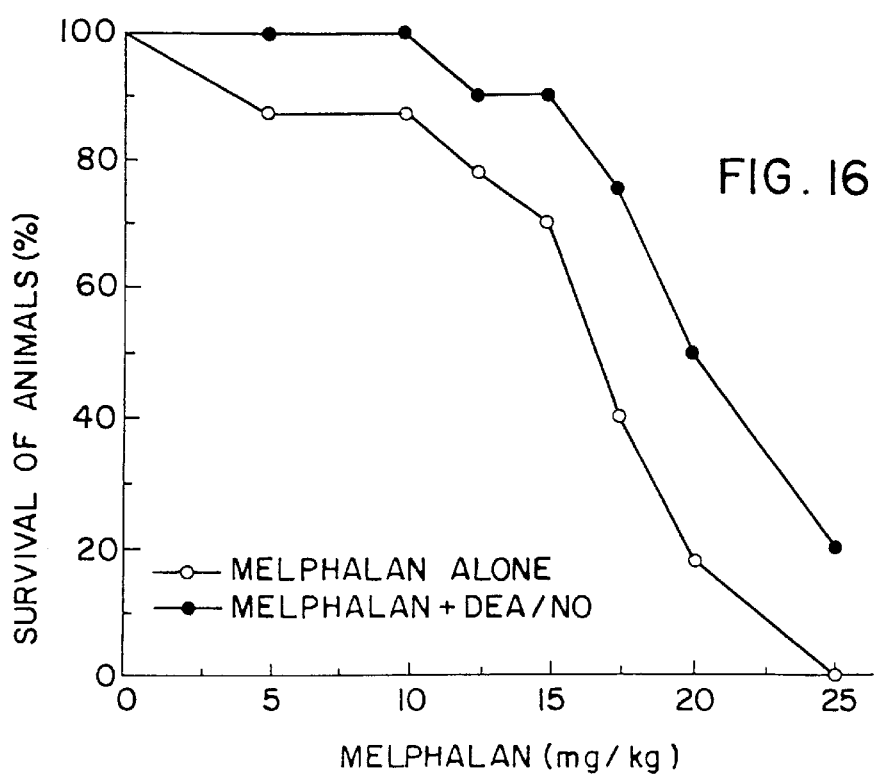
FIG. 16 is a graph of survival of animals (%) versus melphalan dose (mg/kg) showing the chemotherapy survival curves for mice treated with varying doses of melphalan in the absence or presence of 70 mg/kg DEA/NO.

FIG. 16 is a graph of % survival of animals versus does of melphalan (mg/kg) showing the chemotherapy survival curves for mice exposed to melphalan in the absence or presence of DEA/NO. As shown in FIG. 16, DEA/NO protected the mice against the effects of melphalan. DEA/NO provided approximately a 1.2 protection factor at the 50% survival level.

EXAMPLE 16

This example demonstrates that nitric oxide-releasing compounds, such as DEA/NO, can enhance survival of animals undergoing chemotherapy.

Female C3H mice with embryonal ovarian carcinoma (EOC) ascites tumors were generated by intraperitoneal injection of $1.0 \times 10^5$ EOC cells at 10 weeks. Eight days later, when ascites were grossly evident, the animals were injected intraperitoneally with phosphate-buffered saline (PBS) as a control, melphalan (6.25 mg/kg), or melphan in combination with DEA/NO (70 mg/kg). Animals were assessed daily for survival.

Figure 17:
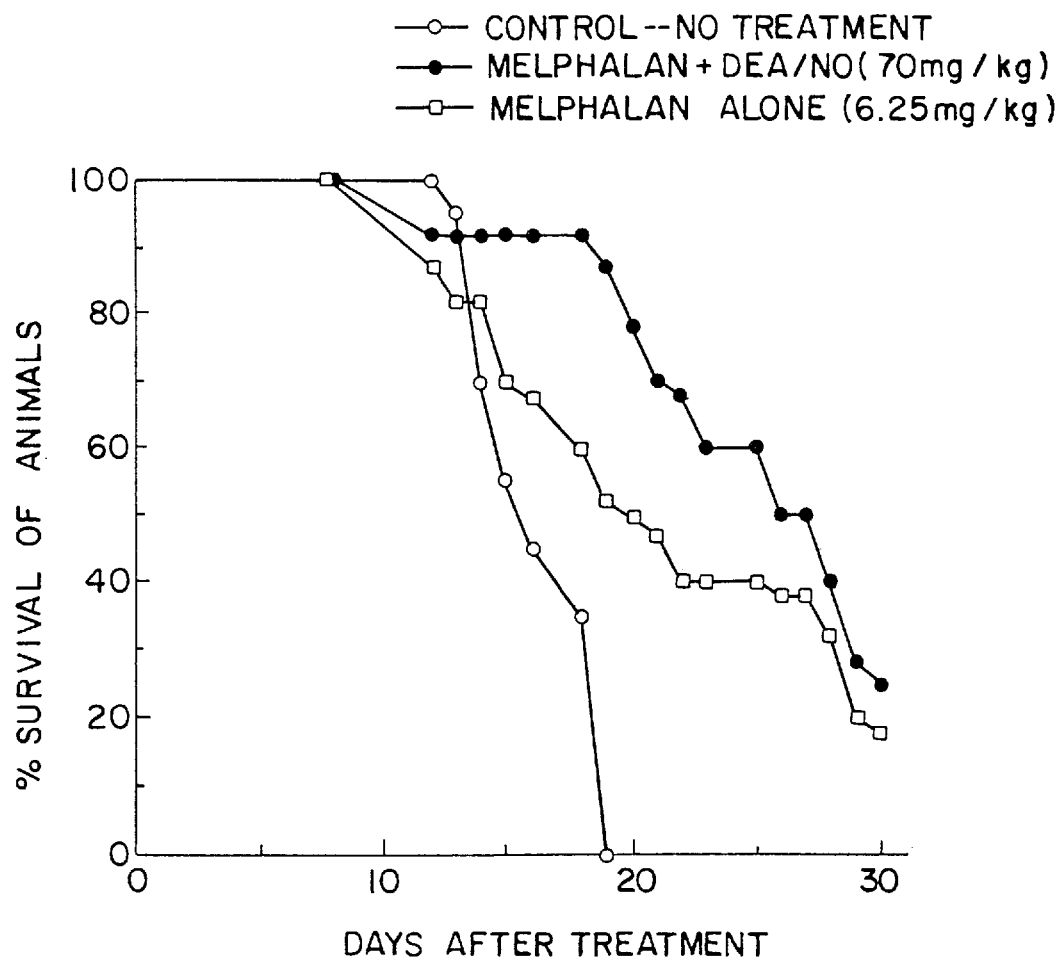
FIG. 17 is a graph of % survival of animals versus days after treatment with 6.25 mg/kg melphalan in the presence or absence of 70 mg/kg DEA/NO compared to control cells.

FIG. 17 is a graph of % survival of animals versus days after treatment showing survival curves for animals treated with melphalan in the presence or absence of DEA/NO compared to control animals. Median survival of the control group was 15 days. Median survival of the group of mice treated with melphalan alone was 20 days, whereas median survival of the group of mice treated with melphalan and DEA/NO was 27 days. Overall survival in both treated groups was significantly longer than the control group and overall survival in the melphalan and DEA/NO combined treatment group was significantly longer than the melphalan treated group by log-rank testing. These data indicate that the combination of DEA/NO and melphalan results in a therapeutic gain, i.e., enhanced melphalan anti-tumor effects with protection of normal tissues.

The above data clearly establish that NO is a potent hypoxic mammalian cell radiosensitizer and that NO can be delivered to cells in a controlled and predictable manner by a chemical delivery system, namely the NONOates, such as DEA/NO, in sufficient concentrations to yield significant hypoxic cell radiosensitization.

The above data also clearly establish that NO is a potent noncancerous mammalian cell and tissue radioprotector and that NO can be delivered to noncancerous cells and tissues in a controlled and predictable manner by NONOates in sufficient concentrations to yield significant cell and tissue radioprotection.

The above data further establish that NO is a potent chemotherapy sensitizer and protector and that NO can be delivered by way of the NONOates to yield chemotherapy sensitization or protection as desired.

All references, including publications, patents, and patent applications, cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method of sensitizing hypoxic cells in a tumor in a mammal to ionizing radiation administered during radiotherapy, which method comprises administering to a mammal having a tumor containing hypoxic cells a radiation-sensitizing effective amount of a nitric oxide-containing compound that spontaneously releases nitric oxide under physiological conditions without requiring the presence of oxygen prior to radiotherapy, wherein said compound is a compound of formula O=N—S—R, wherein R is selected from the group consisting of a $C_1$–$C_8$ alkyl, a $C_3$–$C_{10}$ aryl, a $C_4$–$C_{10}$ heterocyclic nitrogen-containing radical, a $C_3$–$C_{10}$ aryl substituted with a $C_1$–$C_3$ alkyl, and a $C_3$–$C_{10}$ cycloalkyl, which R groups may be substituted by 1–3 substituents, which may be the same or different and are selected from the group consisting of halo, hydroxy, $C_1$–$C_8$ alkoxy, amino, amido, formyl, carboxy, and nitro.

2. A method of sensitizing hypoxic cells in a tumor in a mammal to ionizing radiation administered during radiotherapy, which method comprises administering to a mammal having a tumor containing hypoxic cells a radiation-sensitizing effective amount of a nitric oxide-containing compound that spontaneously releases nitric oxide under physiological conditions without requiring the presence of oxygen prior to radiotherapy, wherein said compound is an S-nitroso adduct of a peptide or a protein.

3. The method of claim 2, wherein the S-nitroso adduct is selected form the group consisting of S-nitroso-N-acetyl-penicillamine and S-nitroso-glutathione.

4. A method of protecting noncancerous cells or tissues in a mammal during radiotherapy, which method comprises administering to a mammal in need of radiotherapy a radioprotecting effective amount of a nitric oxide-containing compound that spontaneously releases nitric oxide under physiological conditions without requiring the presence of oxygen prior to radiotherapy, wherein said compound is a compound of formula O=N—S—R, wherein R is selected from the group consisting of a $C_1$–$C_8$ alkyl, a $C_3$–$C_{10}$ aryl, a $C_4$–$C_{10}$ heterocyclic nitrogen-containing radical, a $C_3$–$C_{10}$ aryl substituted with a $C_1$–$C_3$ alkyl, and a $C_3$–$C_{10}$ cycloalkyl, which R groups may be substituted by 1–3 substituents, which may be the same or different and are selected from the group consisting of halo, hydroxy, $C_1$–$C_8$ alkoxy, amino, amido, formyl, carboxy, and nitro.

5. A method of protecting noncancerous cells or tissues in a mammal during radiotherapy, which method comprises administering to a mammal in need of radiotherapy a radioprotecting effective amount of a nitric oxide-containing compound that spontaneously releases nitric oxide under physiological conditions without requiring the presence of oxygen prior to radiotherapy, wherein the nitric oxide-containing compound is an S-nitroso adduct of a peptide or a protein.

6. The method of claim 5, wherein the S-nitroso adduct is selected from the group consisting of S-nitroso-N-acetylpenicillamine and S-nitro-glutathione.

\* \* \* \* \*